US006872536B1

(12) United States Patent
Roe et al.

(10) Patent No.: US 6,872,536 B1
(45) Date of Patent: Mar. 29, 2005

(54) CHEMOTACTIC PEPTIDE ANTAGONISTS FOR IMAGING SITES OF INFLAMMATION

(75) Inventors: David Roe, Rockwood (CA); Christine Maria Ribic, Hamilton (CA); Betty Chee-Ion Lawrence, Brossard (CA); Catherine Michelle Pollock, Etobicoke (CA); Alfred Pollack, Ljubjana (SI)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 09/437,701

(22) Filed: Nov. 10, 1999

(30) Foreign Application Priority Data

Nov. 10, 1998 (CA) .............................................. 2253911
Nov. 19, 1998 (CA) .............................................. 2266233

(51) Int. Cl.[7] ......................... A61K 38/04; G01N 33/53
(52) U.S. Cl. ............................... 435/7.1; 435/DIG. 35; 530/329; 530/330; 530/331
(58) Field of Search .......................... 435/7.1, DIG. 35; 530/329–331; 514/2

(56) References Cited

U.S. PATENT DOCUMENTS 5,480,970 A * 1/1996 Pollak et al. ................ 530/328
5,789,555 A 8/1998 Pollak et al. .................. 534/14

FOREIGN PATENT DOCUMENTS

| EP | 0398143 | * 11/1990 |
| WO | 9517419 | * 6/1995 |
| WO | 9714443 | * 4/1997 |

OTHER PUBLICATIONS

Baidoo et al., Bioconj. Chem. vol. 9 (Feb. 1998) pp. 208–217.*
Francis et al. JACS vol. 118, No. 37 (1996) pp. 8983–8984.*
Ali H., Richardson R.M., Tomhave E.D., Didsbury J.R. & Snyderman R. (1993). Differences in phosphorylation of formylpeptide and C5a chemoattractant receptors correlate with differences in desensitization. *JBiol. Chem.*, 268, 24247–24254.
Amatruda T.T., Dragas–Graonic S., Holmes R. & Perez H.D. (1995). Signal transduction by the formyl peptide receptor. Studies using chimeric receptors and site–directed mutagenesis define a novel domain for interaction with G–proteins. *J. Bio Chem.*, 270, 28010–28013.
Aswanikumar S., Corcoran B., Schiffmann E., Day A.R., Freer R.J., Showell H.J. & Becker E.L. (1977). Demonstration of a receptor on rabbit neutrophils for chemotactic peptides, *Biochem.Biophys.Res.Commun.*, 74, 810–817.
Babich J.W., Solomon H., Pike M.C., Kroon D., Graham W., Abrams M.J., Tompkins R.G., Rubin R.H. & Fischman A.J. (1993). Technetium–99m–labeled hydrazino nicotinamide derivatized chemotactic peptide analogs for imaging focal sites of bacterial infection. *J.Nucl.Med.*, 34, 1964–1974.

Babich J.W., Graham W., Barrow S.A., Dragotakes S.C., Tompkins R.G., Rubin R.H. & Fischman A.J. (1993). Technetium–99m–labeled chemotactic peptides: comparison with indium–111–labeled white blood cells for localizing acute bacterial infection in the rabbit. *J.Nucl.Med.*, 34, 2176–2181.
Babich J.W., Tompkins R.G., Graham W., Barrow S.A. & Fischman A.J. (1997). Localization of radiolabeled chemotactic peptide at focal sites of *Escherichia coli* infection in rabbits: evidence for a receptor–specific mechanism [see comments]. *J.Nucl.Med.*, 38,1316–1322.
Baggiolini M., Boulay F., Badwey J.A. & Curnutte J.T. (1993). Activation of neutrophil leukocytes: chemoattractant receptors and respiratory burst. *FASEB J.*, 7, 1004–1010.
Bentwood B.J. & Henson P.M. (1980). The sequential release of granule constituents from human neutrophils. *J.Immunol.*, 124, 855–862.
Boulay F., Tardif M., Brouchon L. & Vignais P. (1990). The human N–formlypeptide receptor. Characterization of two cDNA isolates and evidence for a new subfamily of G–protein–coupled receptors. *Biochemistry*, 29, 11123–11133.
Carp, H. (1982). Mitochondrial N–formylmethionyl proteins as chemoattractants for neutrophils. *J. Exp. Med.*, 155, 264–275.
Chatham W.W., Turkiewicz A. & Blackburn W.D.J. (1994). Determinants of neutrophil HOCI generation: ligand–dependent responses and the role of surface adhesion. *J.Leukoc-.Biol.*, 56, 654–660.
Chen Q., Banick P.D. & Thom S.R. (1996). Functional inhibition of rat polymorphonuclear leukocyte B2 integrins by hyperbaric oxygen is associated with impaired cGMP synthesis. *J.Pharmacol.Exp.Ther.*, 276, 929–933.
Day A.R., Pinon D., Muthukumaraswamy N. & Freer R.J. (1980). Synthesis of several chemotactic peptide antagonists. *Peptides*, 1, 289–291.
Derian C.K., Solomon H.F., Higgins J.D., Beblavy M.J., Santulli R.J., Bridger G.J., Pike M.C., Kroon D.J. & Fischman A.J. (1996). Selective inhibition of N–formylpeptide–induced neutrophil activation by carbamate–modified peptide analogues. *Biochemistry*, 35, 1265–1269.

(Continued)

Primary Examiner—Bennett Celsa
(74) *Attorney, Agent, or Firm*—Kramer, Levin, Naftalis & Frankel LLP

(57) ABSTRACT

Radiopharmaceuticals comprising molecules that target to N-formyl-methionyl-leucy-phenylalanine (fMLF) receptor on leukocytes in order to target sites of inflammation for diagnostic imaging are described. The targeting molecules are attached to capping groups that make the entire molecule either antagonists or weak agonists of fMLF receptor and therefore do not elicit a chemotactic response resulting in neutropenia. The preferred targeting molecule is ReO-Gly-lys(Dimethylgly-t-Butylgly-cys-gly)glu-trp-phe-leu-nle-NHCOcyclopropyl (wherein the peptide sequence NLeu-Leu-Phe-Trp-Glu-Lys-Gly is SEQ. ID No. 1.) The invention also relates to the use of combinatorial chemistry to obtain preferred molecules that target sites of inflammation for diagnostic imaging.

5 Claims, 6 Drawing Sheets

OTHER PUBLICATIONS

Dillon S.B., Verghese M.W. & Snyderman R. (1988). Signal transduction in cells following binding of chemoattractants to membrane receptors. *Virchows Arch.B.Cell Pathol.Incl.Mol.Pathol.,* 55, 65–80.

English D. & Lukens J.N. (1983). Regulation of neutrophil inflammatory mediator release: chemotactic peptide activation of stimulus–dependent cytotoxicity. *J.Immunol.,* 130, 850–856.

Fay S.P., Domalewski M.D. & Sklar L.A. (1993). Evidence for protonation in the human neutrophil formyl peptide receptor binding pocket. *Biochemistry,* 32, 1627–1631.

Fischman, A.J., Babich, J.W., & Rubin, R.H. (1994). Infection imaging with technetium–99m–labeled chemotactic peptide analogs. *Semin. Nucl. Med.,* 24, 154–168.

Fischman A.J., Pike M.C., Kroon D., Fucello A.J., Rexinger D., Ten K.C., Wilkinson R., Rubin R.H. & Strauss H.W. (1991). Imaging focal sites of bacterial infection in rats with indium–111–labeled chemotactic peptide analogs [see comments]. *J.NuclMed.,* 32, 483–491.

Follin P., Johansson A. & Dahlgren C. (1991). Intracellular production of reactive oxygen species in human neutrophils following activation by the soluble stimuli FMLP, dioctanoylglycerol and ionomycin. *Cell Biochem Funct.,* 9, 29–37.

Freer R.J., Day A.R., Radding J.A., Schiffmann E., Aswanikumar S., Showell H.J. & Becker E.L. (1980). Further studies on the structural requirements for synthetic peptide chemoattractants. *Biochemistry,* 19, 24042410.

Freer R.J., Day A.R., Muthukumaraswamy N., Pinon D., Wu A., Showell H.J. & Becker E.L. (1982). Formyl peptide chemoattractants: a model of the receptor on rabbit neutrophils. *Biochemistry,* 21, 257–263.

Gao J.L., Becker E.L., Freer R.J., Muthukumaraswamy N. & Murphy P.M. (1994). A high potency nonformylated peptide agonist for the phagocyte N–formylpeptide chemotactic receptor. *J.Exp.Med.,* 180, 2191–2197.

Hampton M.B., Kettle A.J. & Winterbourn C.C. (1996). Involvement of superoxide and myeloperoxidase in oxygen–dependent killing of *Staphylococcus aureus* by neutrophils. *Infect.Immun.,* 64, 3512–3517.

Higgins J.D., Bridger G.J., Der'Ian C.K., Beblavy M.J., Hernandez P.E., Gaul F.E., Abrams M.J., Pike M.C. & Solomon H.F. (1996). N–terminus urea–substituted chemotactic peptides: new potent agonists and antagonists toward the neutrophil fMLF receptor. *J.Med.Chem.,* 39, 1013–1015.

Ho P.P., Young A.L. & Southard G.L. (1978). Methyl ester of N–formylmethionyl–leucyl–phenylalanine: chemotactic responses of human blood monocytes and inhibition of gold compounds. *Arthritis Rheum.,* 21, 133–136.

Hoffman J.F., Keil M.L., Riccobene T.A., Omann G.M. & Linderman J.J. (1996a). Interconverting receptor states at 4 degrees C for the neutrophil N–formyl peptide receptor. *Biochemistry,* 35, 13047–13055.

Jesaitis A.J., Naemura J.R., Sklar L.A., Cochrane C.G. & Painter R.G. (1984). Rapid modulation of N–formyl chemotactic peptide receptors on the surface of human granulocytes: formation of high–affinity ligand–receptor complexes in transient association with cytoskeleton. *J.Cell Biol,* 98, 1378–1387.

Johansson B., Wymann M.P., Holmgren–Peterson K. & Magnusson K.E. (1993). N–formyl peptide receptors in human neutrophils display distinct membrane distribution and lateral mobility when labeled with agonist and antagonist. *J. Cell Biol.,* 121, 1281–1289.

Kalmar, J & Van Dyke, T. (1994). Effect of Bacterial Products on Neutrophil Chemotaxis. *Meth. Enzym.,* 236, 58–87.

Kanamori Y., Niwa M., Kohno K., Al–Essa L.Y., Matsuno H., Kozawa O. & Uematsu T. (1997). Migration of neutrophils from blood to tissue: alteration of modulatory effects of prostanoid on superoxide generation in rabbits and humans. *Life Sci.,* 60, 1407–1417.

Korchak H.M., Wilkenfeld C., Rich A.M., Radin A.R., Vienne K. & Rutherford L.E. (1984). Stimulus response coupling in the human neutrophil. Differential requirements for receptor occupancy in neutrophil responses to a chemoattractant. *J.Biol.Chem.,* 259, 7439–7445.

Luscinskas, F. W., Cybulsky, M. I., Kiely, J. M., Peckins, C.S., Davis, V.M. & Gimbrone, M.A. (1991). Cytokine–activated human endothelial monolayers support enhanced neutrophil transmigration via a mechanism involving both endothelial leukocyte adhesion molecule–1 and intercellular adhesion molecule–1. *J. Immunol.,* 146, 1617–1625.

Marasco W.A., Fantone J.C., Freer R.J. & Ward P.A. (1983). Characterization of the rat neutrophil formyl peptide chemotaxis receptor. *Am.JPathol.,* 111, 273281.

McKay D.A., Kusel J. R. & Wilkinson P.C. (1991). Studies of chemotactic factor–induced polarity in human neutrophils. Lipid mobility, receptor distribution and the time–sequence of polarization. *J. Cell Sci.,* 100 (Pt 3), 473–479.

Miettinen H.M., Mills J.S., Gripentrog J.M., Dratz E.A., Granger B.L. & Jesaitis A.J. (1997). The ligand binding site of the formyl peptide receptor maps in the transmembrane region. *J.Immunol.,* 159, 4045–4054.

Miyasaki K.T., Song J.P. & Murthy R.K. (1991). Secretion of myeloperoxidase isoforms by human neutrophils. *Anal.Biochem.,* 193, 38–44.

Mueller H., Weingarten R., Ransnas L.A., Bokoch G.M. & Sklar L.A. (1991). Differential amplification of antagonistic receptor pathways in neutrophils. *J.Biol.Chem.,* 266, 12939–12943.

Niedel J., Wilkinson S. & Cuatrecasas P. (1979). Receptor–mediated uptake and degradation of 1251–chemotactic peptide by human neutrophils. *J. Biol. Chem.,* 254, 10700–10706.

Nunoi H., Endo F., Chikazawa S. & Matsuda I. (1985). Regulation of receptors and digestive activity toward synthesized formyl–chemotactic peptide in human polymorphonuclear leukocytes. *Blood,* 66, 106–114.

Painter R.G. & Aiken M.L. (1995). Regulation of N–formyl– methionyl–leucyl–phenylalanine receptor recycling by surface membrane neutral endopeptidase–mediated degradation of ligand. *J.Leukoc.Biol.,* 58, 468–476.

Palmblad J. (1984). The role of granulocytes in inflammation. *Scand.J.Rheumatol.,* 13, 163–172.

Perez H.D., Elfman F., Marder S., Lobo E. & Ives H.E. (1989). Formyl peptide–induced chemotaxis of human polymorphonuclear leukocytes does not require either marked changes in cytosolic calcium or specific granule discharge. Role of formyl peptide receptor reexpression (or recycling). *J.Clin.Invest.,* 83, 1963–1970.

Prossnitz E.R. & Ye R.D. (1997). The N–formyl peptide receptor: a model for the study of chemoattractant receptor structure and function. *Pharmacol.Ther.,* 74, 73–102.

Prossnitz E.R. (1997). Desensitization of N–formylpeptide receptor–mediated activation is dependent upon receptor phosphorylation. *J.Biol.Chem.,* 272, 15213–15219.

Radel S.J., Genco R.J. & De N. E. (1994). Structural and functional characterization of the human formyl peptide receptor ligand–binding region. *Infect. Immun.,* 62, 1726–1732.

Remes J., Petaja–Repo U. & Rajaniemi H. (1994). Internalization of N–formyl peptide chemotactic receptor–ligand complex by human neutrophils. The role of the receptor's 2–kDa external domain and carbohydrates. *J.Recept.Res.,* 14, 4762.

Remes J.J., Petaja–Repo U.E. & Rajaniemi H.J. (1991). Rat and human neutrophil N–formyl–peptide chemotactic receptors. Species difference in the glycosylation of similar 35–38 kDa polypeptide cores. *Biochem.J.,* 277 (Pt 1), 67–72.

Ribeiro R.A., Souza–Filho M.V., Souza M.H., Oliveira S.H., Costa C.H., Cunha F.Q. & Ferreira H.S. (1997). Role of resident mast cells and macrophages in the neutrophil migration induced by LTB4, fMLP and C5a des arg. *Int.Arch.Allergy Immunol.,* 112, 27–35.

Schiffmann, E., Corcoran, B.A. and Whale, S.M. (1975). N–formylmethionylpeptides as chemoattractants for leukocytes. *Proc.Natl.Acad.Sci. USA* 72,1059–1062.

Schreiber R.E., Prossnitz E.R., Ye R.D., Cochrane C.G. & Bokoch G.M. (1994). Domains of the human neutrophil N–formyl peptide receptor involved in G protein coupling. Mapping with receptor–derived peptides. *J.Biol.Chem.,* 269, 326–331.

Sepe S.M. & Clark R.A. (1985). Oxidant membrane injury by the neutrophil myeloperoxidase system. I. Characterization of a liposome model and injury by myeloperoxidase, hydrogen peroxide, and halides. *J.Immunol.,* 134, 1888–1895.

Skalak R., Skierczynski B.A., Wung S.L., Chien S. & Usami S. (1993). Mechanical models of pseudopod formation. *Blood Cells,* 19, 389–397.

Sklar L.A., Finney D.A., Oades Z.G., Jesaitis A.J., Painter R.G. & Cochrane C.G. (1984). The dynamics of ligand–receptor interactions. Real–time analyses of association, dissociation, and internalization of an N–formyl peptide and its receptors on the human neutrophil. *J.Biol.Chem.,* 259, 5661–5669.

Sklar L.A., Sayre J., McNeil V.M. & Finney D.A. (1985). Competitive binding kinetics in ligand–receptor–competitor systems. Rate parameters for unlabeled ligands for the formyl peptide receptor. *Mol.Pharmacol.,* 28, 323–330.

Sklar L.A., Fay S.P., Seligmann B.E., Freer R.J., Muthukumaraswamy N. & Mueller H. (1990). Fluorescence analysis of the size of a binding pocket of a peptide receptor at natural abundance. *Biochemistry,* 29, 313–316.

Snyderman R. (1983). Pharmacologic manipulation of leukocyte chemotaxis. Present knowledge and future trends. *Am.J.Med.,* 75, 10–18.

Spisani S., Traniello S., Giuliani A.L., Torrini I., Pagani Z.G., Paglialunga P.M., Gavuzzo E., Mazza F., Pochetti G. & Lucente G. (1992). New chemotactic peptide analogs with high biological activity for human neutrophils. *Biochem.Int.,* 26, 1125–1135.

Srinivasan R., Buchweitz J.P. & Ganey P.E. (1997). Alteration by flutamide of neutrophil response to stimulation. Implications for tissue injury. *Biochem. Pharmacol.,* 53, 1179–1185.

Tae, H. J., Grossmann, M. and Inhae, J. (1998). G protein–coupled receptors. Diversity of receptor–ligand interactions. *J. Biol. Chem.,* 273 (28), 17299–17302.

Tardif M., Mery L., Brouchon L. & Boulay F. (1993). Agonist–dependent phosphorylation of N–formylpeptide and activation peptide from the fifth component of C (C5a) chemoattractant receptors in differentiated HL60 cells. *J.Immunol.,* 150, 3534–3545.

Toniolo C., Crisma M., Moretto V., Freer R.J. & Becker E.L. (1990). N alpha–formylated and tert–butyloxycarbonylated Phe–(Leu–Phe)n and (Leu–Phe)n peptides as agonists and antagonists of the chemotactic formylpeptide receptor of the rabbit peritoneal neutrophil. *Biochim.Biophys.Acta,* 1034, 67–72.

Toniolo C., Crisma M. & Becker E.L. (1990). Replacement of the N alpha–blocking group in the formyl–methionyl tripeptide chemoattractant: an insight into the mode of binding at the receptor on rabbit neutrophils. *Farmaco.,* 45, 921–925.

Vallabhajousula, S. (1997). Technetium–99m–Labeled Chemotactic Peptides: Specific for imaging Infection? *J. Nuc. Med.,* 38, 1322–1326.

Van Der Laken CJ, Boerman O.C., Oyen W.J., Van De Ven MT, Edwards D.S., Barrett J.A., Van Der Meer JW & Corstens F.H. (1997). Technetium–99m–labeled chemotactic peptides in acute infection and sterile inflammation [see comments]. *J.Nucl.Med.,* 38, 1310–1315.

Wang J.P., Tsao L.T., Raung S.L. & Lin C.N. (1997). Investigation of the inhibitory effect of broussochalcone A on respiratory burst in neutrophils. *Eur.J.Pharmacol.,* 320, 201–208.

Weiss, S.J., Peppin, G., Ortiz, X., Ragsdale, C., Test, S.T. (1983). Oxidative autoactivation of latent collagenase by human neutrophils. *Science,* 227, 747–749.

Williams L.T., Snyderman R., Pike M.C. & Lefkowitz R.J. (1977). Specific receptor sites for chemotactic peptides on human polymorphonuclear leukocytes. *Proc.Natl.Acad. Sci. U.S.A.,* 74, 1204–1208.

Winterbourn C.C., Pichorner H. & Kettle A.J. (1997). Myeloperoxidase–dependent generation of a tyrosine peroxide by neutrophils. *Arch. Biochem. Biophys.,* 338, 15–21.

Wong, E., Fauconnier, T., Bennett, S., Valliant, J., Nguyen, T., Lau, F., Lu, L.F.L., Pollak, A., Bell, R.A. and Thornback, J.R. (1997). Rhenium(V) and Technetium(V) Oxo Complexes of an $N_2N'S$ Peptide Chelator: Evidence of Interconversion between the Syn and Anti Conformations. *Inorg. Chem.,* 36, 5799–5808.

* cited by examiner

SEQUENCE LISTING

<160> NUMBER OF SEQ ID NOS: 10

<210> SEQ ID NO 1
<211> LENGTH: 7
<212> TYPE: PRT
<213> ORGANISM: Artificial
<220> FEATURE:
<223> OTHER INFORMATION: Description of Artificial Sequence: The peptide
      can be synthesized via solid pahse synthesis on an automated
      synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 1

Leu Leu Phe Trp Glu Lys Gly
1               5

<210> SEQ ID NO 2
<211> LENGTH: 7
<212> TYPE: PRT
<213> ORGANISM: Artificial
<220> FEATURE:
<223> OTHER INFORMATION: Description of Artificial Sequence:  The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 2

Leu Leu Phe Ser Glu Lys Gly
1               5

<210> SEQ ID NO 3
<211> LENGTH: 7
<212> TYPE: PRT
<213> ORGANISM: Artificial
<220> FEATURE:
<223> OTHER INFORMATION: Description of Artificial Sequence:  The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 3

```
Leu Leu Phe Tyr Glu Lys Gly
1               5

<210> SEQ ID NO 4
<211> LENGTH: 7
<212> TYPE: PRT
<213> ORGANISM: Artificial
<220> FEATURE:
<223> OTHER INFORMATION: Description of Artificial Sequence:  The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 4

Leu Leu Phe Trp His Lys Gly
1               5

<210> SEQ ID NO 5
<211> LENGTH: 7
<212> TYPE: PRT
<213> ORGANISM: Artificial
<220> FEATURE:
<223> OTHER INFORMATION: Description of Artificial Sequence:
      The peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 5

Leu Leu Phe Ser His Lys Gly
1               5

<210> SEQ ID NO 6
<211> LENGTH: 7
<212> TYPE: PRT
<213> ORGANISM: Artificial
<220> FEATURE:
<223> OTHER INFORMATION: Description of Artificial Sequence:  The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 6

Leu Leu Phe Tyr His Lys Gly
```

-continued

```
<210> SEQ ID NO 7
<211> LENGTH: 7
<212> TYPE: PRT
<213> ORGANISM: Artificial
<220> FEATURE:
<223> OTHER INFORMATION: Description of Artificial Sequence:  The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 7

Leu Leu Phe Trp Lys Lys Gly
1               5

<210> SEQ ID NO 8
<211> LENGTH: 7
<212> TYPE: PRT
<213> ORGANISM: Artificial
<220> FEATURE:
<223> OTHER INFORMATION: Description of Artificial Sequence:  The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 8

Leu Leu Phe Ser Lys Lys Gly
1               5

<210> SEQ ID NO 9
<211> LENGTH: 7
<212> TYPE: PRT
<213> ORGANISM: Artificial
<220> FEATURE:
<223> OTHER INFORMATION: Description of Artificial Sequence:  The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an to
      chemotaxis.
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 9

Leu Leu Phe Tyr Lys Lys Gly
1               5
```

```
<210> SEQ ID NO 10
<211> LENGTH: 7
<212> TYPE: PRT
<213> ORGANISM: Artificial
<220> FEATURE:
<223> OTHER INFORMATION: Description of Artificial Sequence: The
      peptide can be synthesized via solid pahse synthesis on an
      automated synthesizer.  The first Leu in the sequence is NLeu.
<220> FEATURE:
<221> NAME/KEY: BINDING
<222> LOCATION: (1)..(1)
<223> OTHER INFORMATION: Contains an amino group which is bound to a
      capping group.  The capping group makes the compound an
      antagonist or a weak agonist to chemotaxis.
<220> FEATURE:
<221> NAME/KEY: MISC_FEATURE
<222> LOCATION: (4)..(5)
<223> OTHER INFORMATION: Xaa=any amino acid
<220> FEATURE:
<221> NAME/KEY: BINDING
<222> LOCATION: (6)..(6)
<223> OTHER INFORMATION: Binding site for a chelator which is capable of
      complexing a radionuclide metal.

<400> SEQUENCE: 10

Leu Leu Phe Xaa Xaa Lys Gly
1               5
```

CHEMOTACTIC PEPTIDE ANTAGONISTS FOR IMAGING SITES OF INFLAMMATION

FIELD OF THE INVENTION

The present invention relates to diagnostic imaging of the sites of inflammation in humans and animals. More particularly, the present invention relates to the use of combinatorial chemistry to identify targeting molecules which bind to receptors on cells that accumulate at sites of inflammation.

BACKGROUND OF THE INVENTION

The art of diagnostic imaging exploits contrasting agents that in binding or localizing a site selectively within the body, help to resolve the image of diagnostic interest. $^{67}$Gallium salts, for example, have an affinity for tumours and infected tissue. With the aid of scanning tomography, $^{87}$Gallium salts can reveal afflicted body regions to the physician. Other contrasting agents include metal radionuclides such as $^{99}$technetium and $^{186/188}$rhenium. These have been used to label targeting molecules such as proteins, peptides and antibodies that localize at desired regions of the human body.

It is critical for the management of patient care to have the ability to quickly and accurately identify sites of infection and resultant inflammation. Current radionuclide labeled targeting molecules for targeting sites of infection and resultant inflammation bind to leukocytes (white blood cells). These targeting molecules do not provide prompt diagnosis due to delays of up to 12–24 hours following injection. These delays occur because the targeting molecules require the separation of leukocytes from the patents whole blood before radiolabeling. Further delays result because after re-injection the leukocytes take several hours before they can re-localize to the sites of inflammation. Other targeting molecules have high molecular weight which results in slow delivery of the radiopharmaceutical to the sites of inflammation.

The problem with time delays can be overcome by using radiopharmaceuticals that bind well to N-formyl-methionylleucyl-phenylalanine (fMLF) receptor on leukocytes. This receptor is also referred to as formyl peptide receptor (FPR). The accumulation of leukocytes at sites of inflammation is the primary mechanism by which the immune system localizes and destroys microbial and other toxic agents. Radiopharmaceuticals that bind to fMLF receptor can label leukocytes that are present in circulation as well as those at sites of inflammation. This allows for prompt diagnosis.

fMLF is a bacterial product that initiates leukocyte chemotaxis by binding to high affinity fMLF receptors present on polymorphonuclear leukocytes (PMNs) and mononuclear phagocytes. Chemotaxis refers to the migration of leukocytes to sites of inflammation and infection. Current targeting molecules that that bind well to fMLF receptor are agonists for this receptor. These targeting molecules therefore elicit an accumulation of leukocytes in healthy tissue that causes tissue damage. This effect is called neutropenia. This is a significant problem.

Most known chemotactic antagonists however exhibit low binding affinity to the fMLF receptor. None have a group that is suitable for transporting a radionuclide that is essential for radioimaging applications.

There is therefore a need for radiopharmaceuticals that have a high affinity for the fMLF receptor so that they can target leukocytes that accumulate at sites of inflammation. There is a further need for such radiopharmaceuticals that are antagonists or very weak agonists of chemotaxis in order to eliminate problems such as neutropenia that are associated with agonists.

Recent studies have indicated that the binding affinity of targeting peptides and the chemotactic functionality of those targeting peptides depend on two different factors. The three amino acid residues at the N-terminus of the peptides (methionine, leucine and phenylalanine) mainly govern the degree of binding of the targeting peptide to the receptor. There is also a contribution from amino acid residues that are more removed from this site. The functional group attached to the N-terminus of the peptides has a large affect on the chemotactic functionality of the peptide when bound to the receptor. For example the presence of a formyl group or an acetyl group has been shown to provide agonist or weak agonist activity whereas a tertbutoxycarbonyl group causes the peptide to exhibit antagonist activity but with low affinity binding.

There is therefore a need for a radiopharmaceutical that is a chemotactic antagonist with an N-terminus capping group and a structure that confers a strong binding affinity for the fMLF receptor to the radio pharmaceutical.

SUMMARY OF THE INVENTION

The invention relates to radiopharmaceuticals that are capable of complexing a radionuclide metal and that has a high binding affinity for fMLF receptor. The radiopharmaceuticals of the present invention are antagonists or weak agonists of chemotaxis.

The invention includes metal-containing molecules that are capable of binding to the fMLF receptor. The invention also includes molecules that contain a region complexed to transition metals. The presence of the metal within the molecule allows for the accumulation of the metal at sites of inflammation or infection, since the whole molecule binds to receptors upregulated on leukocytes that accumulate at these sites, and thus allows for the detection of inflammation or infection.

According to one aspect of the present invention, there is provided a combinatorial library for obtaining compounds that target sites of inflammation comprising a mixture molecules of the following formula I:

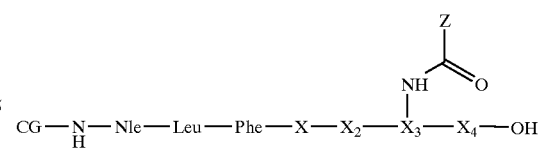

wherein CG is a capping group that makes the compound an antagonist or a weak agonist to chemotaxis; X, X2, X3 and X4 are amino acids selected from natural and unnatural amino acids; Z is a chelator capable of complexing a radionuclide metal or a chelator attached to a radionuclide metal, X3 being a site of attachment for said chelator.

According to another aspect of the present invention, there is provided a compound for binding to sites of sites of inflammation having the following formula I:

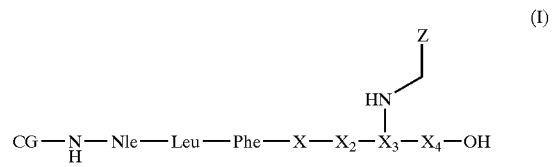

wherein CG is a capping group that makes the compound an antagonist or a weak agonist to chemotaxis; X, X2, X3 and X4 are amino acids selected from natural and unnatural amino acids; Z is a chelator capable of complexing a radionuclide metal or a chelator attached to a radionuclide metal, X3 being a site of attachment for said chelator.

According to a particular aspect of the invention there are provided compounds of formula II:

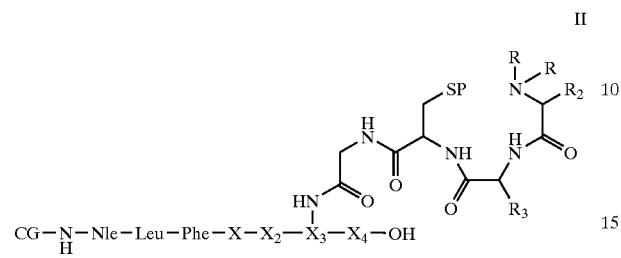

II wherein CG is a capping group that makes the compound an antagonist or a weak agonist to chemotaxis; X, X2, X3 and X4 are amino acids selected from natural and unnatural amino acids; X3 being a site of attachment for said chelator; R, and R2 is a linear or branched, saturated or unsaturated $C_{1-6}$ alkyl chain that is optionally interrupted by one or two heteroatoms selected from N, O, and S; and is optionally substituted by at least one group selected from hydroxyl, amino, carboxyl, $C_{1-8}$ alkyl, aryl and C(O)R; R3 is selected from H; alkyl; an alkyl substituted by a group selected from amino, aminoacyl, carboxyl, guaniginyl, hydroxyl, thiol, phenyl, phenolyl, indolyl, and imidazolyl;

According to another aspect of the invention there are provided compounds of the formula III:

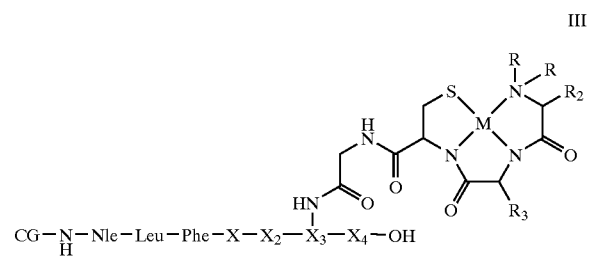

III wherein CG is a capping group that makes the compound an antagonist or a weak agonist to chemotaxis; X, X2, X3 and X4 are amino acids selected from natural and unnatural amino acids; X3 being a site of attachment for said chelator; and R, R2 and R3 are defined as above; M is a metal or an oxide or nitride thereof.

According to yet another aspect of the present invention, there is provided a method of obtaining a compound that targets sites of sites of inflammation comprising the steps of:

I) Preparing a library of compounds of the following formula I:

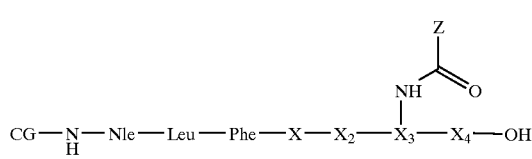

wherein CG is a capping group that makes the compound an antagonist or a weak agonist to chemotaxis; X, X2, X3 and X4 are amino acids selected from natural and unnatural amino acids; Z is a chelator capable of complexing a radionuclide metal , X3 being a site of attachment for said chelator.

II) Preparing mixtures of said compounds comprising different variables of said natural or synthetic amino acids and said capping groups;
III) Testing said mixtures for binding to N-formyl-methionyl-leucyl-phenylalanine (fMLF) receptor;
IV) Selecting mixtures that show positive binding to N-formyl-methionyl-leucyl-phenylalanine (fMLF) receptor; and
V) Deconvoluting said mixtures that show positive binding to N-formyl-methionyl-leucyl-phenylalanine (FMLF) receptor to obtain a compound that binds to N-formyl-methionyl-leucylphenylalanine (fMLF) receptor.

According to another aspect of the invention there is provided a use of the compound of formula I to target and image sites of inflammation in a patient.

The invention also includes a kit comprising compounds of formula I, and suitable reagents for labeling the compounds with a radionuclide metal and delivering the labeled compounds to a patient.

DESCRIPTION OF THE DRAWINGS

FIG. 1 is a bar graph showing competition Binding of Re-library mixtures administered to elicited rat PMNs in the presence of 6 nM $H^3$-fMLF. Data is expressed as a % control of $^3$H-fMLF binding with standard errors being ≦15% in all cases (n=1; replicates of 4). FIG. 1A represents mixtures administered at 10 uM concentrations. The control compound illustrates competition binding by ReORP455 (Re-metal complexed to the (Dimethylgly-t-Butylgly-cys-gly)—chelator) while

DETAILED DESCRIPTION

Figure 1A:
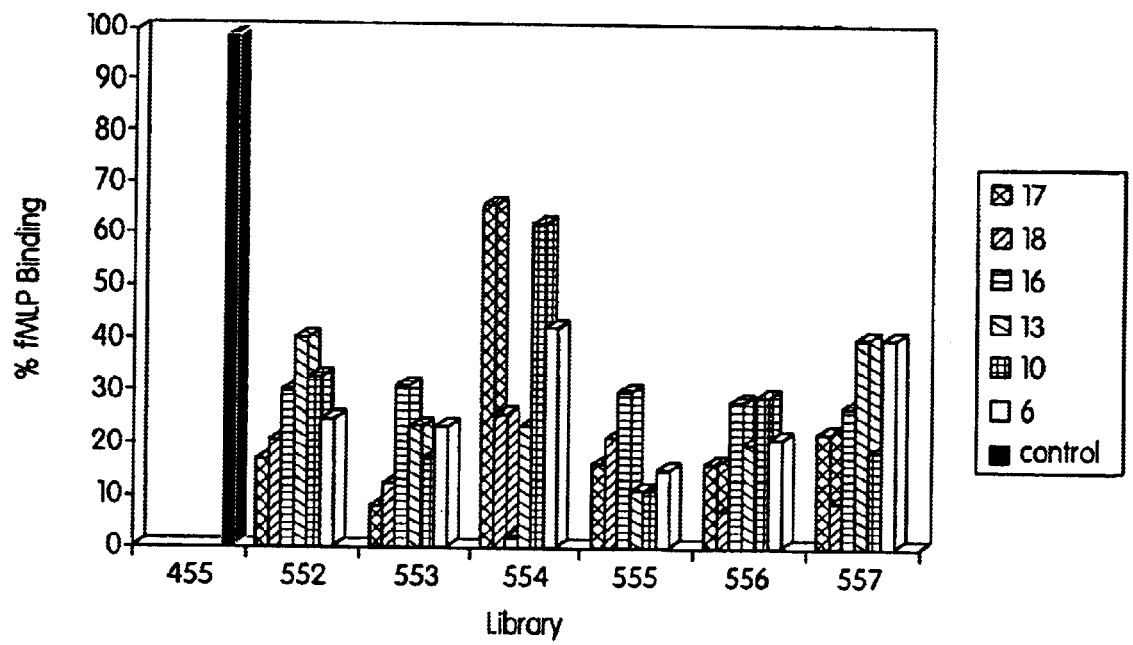

The radiopharmaceuticals of the present invention are molecules that target sites of inflammation. The preferred molecules are peptides that bind fMLF receptor. The molecules include a chelating moiety that complexes radionuclide metals such as $^{99m}$Tc and Re which is isostructural to $^{99m}$Tc. The chelating moiety may play a role in binding fMLF receptor.

The molecules of the present invention have the following formula:

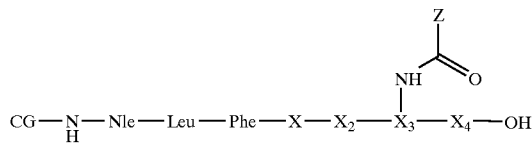

wherein CG is a capping group that makes the compound an antagonist or a weak agonist to chemotaxis; X X2, X3 and X4 are amino acids selected from natural and unnatural amino acids; Z is a chelator capable of complexing a radionucleotide metal or a chelator attached to a radionucleotide metal, X3 being a site of attachment for said chelator (SEQ ID NOS: 1–109).

X3 is the amino acid residue used to attach the metal preferably has three functional groups. Preferably X3 is lysine. Amino acid X3 must have a point of attachment to the growing peptide to facilitate synthesis. Such a moiety allows a suitably protected reagent to react with the amino terminus of the solid supported peptide during the synthesis (in the case of lysine this is the carboxyl group). The residue must also contain a group for the attachment of further amino adds to enable the peptide synthesis to be continued. In the case of the preferred lysine this is the □-amino group of the amino acid. Finally, the reagent must incorporate a functional group for the later attachment of the metal chelating portion of the molecule. This may be any group capable of attaching to a metal chelator and may also be linked to the rest of the residue by aliphatic, aromatic, heteroaromatic, ether or other similar groups. These groups may or may not be involved in the binding of the molecule to the fMLF receptor. In the case of lysine therefore the three groups are carboxyl, amino and amino. In some cases (for example lysine) it may be necessary to optionally protect one or two of the groups to allow selective reactions to take place. Subsequent deprotection will then furnish the required functional group for further reaction.

The preferred amino add for X4 is glycine. Other amino acids may also be used at position X4.

The metal chelating moiety used for the purposes of the present invention includes chelators having the following general formula:

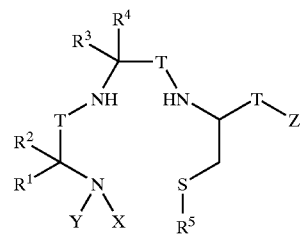

wherein,

X is a linear or branched, saturated or unsaturated $C_{1-6}$ alkyl chain that is optionally interrupted by one or two heteroatoms selected from N, O, and S; and is optionally substituted by at least one group selected from hydroxyl, amino, carboxyl, $C_{1-6}$ alkyl, aryl and C(O)R;

Y is H or a substituent defined by X;

Z is the position of attachment for the targeting portion of the library;

$R^1$ through $R^4$ are selected independently from H; carboxyl; $C_{1-4}$ alkyl; $C_{1-4}$ alkyl substituted with a group selected from hydroxyl, amino, sulfhydryl, halogen, carboxyl, $C_{1-4}$ alkoxycarbonyl and aminocarbonyl; an alpha carbon side chain of a D- or L- amino acid other than proline; and C(O)R;

$R^5$ is selected from H and a sulfur protecting group; and

T is carbonyl or $CH_2$.

Where the chelator is complexed to a metal or a metal radionuclide, the complex has the following general formula:

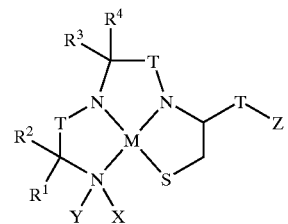

X is a linear or branched, saturated or unsaturated $C_{1-6}$ alkyl chain that is optionally interrupted by one or two heteroatoms selected from N, O, and S; and is optionally substituted by at least one group selected from hydroxyl, amino, carboxyl, $C_{1-6}$ alkyl, aryl and C(O)R;

Y is H or a substituent defined by X;

Z is the position of attachment for the targeting portion of the library;

$R^1$ through $R^4$ are selected independently from H; carboxyl; $C_{1-4}$ alkyl; $C_{1-4}$ alkyl substituted with a group selected from hydroxyl, amino, sulfhydryl, halogen, carboxyl, $C_{1-4}$ alkoxycarbonyl and aminocarbonyl; an alpha carbon side chain of a D- or L- amino acid other than proline; and C(O)R;

T is carbonyl or $CH_2$; and

M is metal for use in diagnostic imaging or an oxide or nitride thereof.

The most preferred chelator for $^{99m}$technetium radiopharmaceuticals is RP455. RP414 may also be used. The structures of RP414 and RP455 are as follows:

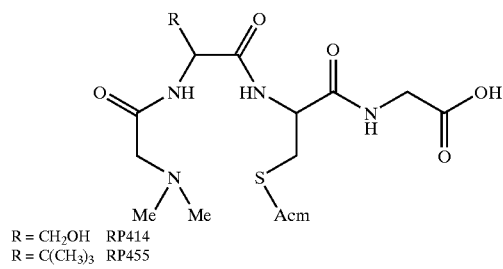

R = CH$_2$OH  RP414
R = C(CH$_3$)$_3$  RP455

Re and Tc complexes of these chelators are isostructural. Also, these chelators are advantageous because the chemistry of these compounds is well understood and they form neutral Re and $^{99m}$Tc complexes. It is possible to label these chelators with Re or $^{99m}$Tc in one easy step. In addition these chelators have the advantage of being applicable for conjugation to a variety of targeting molecules, being compatible with solid phase synthesis.

Labeling of RP414 with $^{99m}$Tc can be carried out either at ambient or elevated temperature, rapidly, and with quantities of chelator approaching stoichiometric amounts. The complex is stable to both acidic and basic conditions and remains unchanged in-vivo.

Other chelators may be used to carry out the invention. The invention is not limited to the preferred chelators listed above.

The chelator moiety of the targeting molecules incorporate a diagnostically useful metal within their structure as a complex. Suitable metals include radionuclides such as technetium and rhenium in various forms such as $^{99m}$TcO$_3^+$, $^{99m}$TcO$_2^+$, ReO$_3^+$, ReO$_2^+$. Incorporation of the metal into the structure of the molecule can be achieved by various methods common in the art of coordination chemistry. In the case where the metal is technetium-99m ($^{99m}$Tc) the following general procedure may be used to generate the technetium-containing molecule. The chelator is dissolved in an aqueous alcohol such as ethanol to form a solution. The solution is then degassed to removed oxygen and the thiol protecting group removed with a suitable reagent, for example sodium hydroxide, and then neutralized with acetic acid. In the labeling step sodium pertechnetate, obtained from a molybdenum generator, is added to the alcoholic solution of the chelator, together with an amount of reducing agent sufficient to reduce the technetium, and the resulting solution heated. The labeled conjugate may be separated from the contaminants $^{99m}$TcO$_4^-$ and colloidal $^{99m}$TcO$_2$ chromatographically, for example with a C-18 sep-pak cartridge.

In an alternative method, labeling may be effected by a transchelation reaction. The technetium source is a solution of technetium complexed with labile ligands facilitating ligand exchange with the selected chelator. Suitable ligands for transchelation are known to one skilled in the art and may include tartrate, citrate, glucoheptonate, and heptagluconate.

In a further alternative method, labeling may be accomplished utilizing a "one-pot" procedure whereby the sulfur protecting group is removed during the labeling process. The molecule having an acetomidomethyl group attached to the sulfur is dissolved in aqueous ethanol. In the labeling step sodium pertechnetate, obtained from a molybdenum generator, is added to the alcoholic solution of the chelator, together with an amount of reducing agent sufficient to reduce the technetium, and the resulting solution heated. The labeled conjugate may be separated from the contaminants $^{99m}$TcO$_4^-$ and colloidal $^{99m}$TcO$_2$ chromatographically, for example with a C-18 sep-pak cartridge.

A different approach to the labeling of the chelators defined above is described in U.S. Pat. No. 5,789,555 and is incorporated herein by reference. The chelator molecules are immobilized on a solid phase support through a linkage that is cleaved upon metal chelation. This is achieved when the chelator is coupled to a functional group of the support by one of the complexing atoms. Preferably a complexing sulfur atom is attached to the support which is functionalized with a sulfur protecting group such as maleimide.

When labeled with a diagnostically useful metal, molecules of the present invention can be used to detect sites of inflammation or infection by procedures established by one skilled in the art of diagnostic imaging. Thus a molecule containing a metal such as $^{99m}$Tc may be administered to a mammal by intravenous injection in a pharmaceutically acceptable solution such as isotonic saline. The amount of metal-containing molecule appropriate is dependent upon the distribution profile of the chosen molecule in the sense that a compound that is cleared rapidly may be administered in higher doses than a molecule that clears less rapidly. Unit doses acceptable for imaging inflammation or infection are in the range of about 5–40 mCi for a 70 kg individual. In vivo distribution and localization is tracked by standard scintigraphic techniques at an appropriate time subsequent to the injection—typically between 30 minutes and 180 minutes depending upon the rate of accumulation at the target site with respect to the rate of clearance at non-target tissue.

Capping groups within the scope of the present invention include but are not limited to:

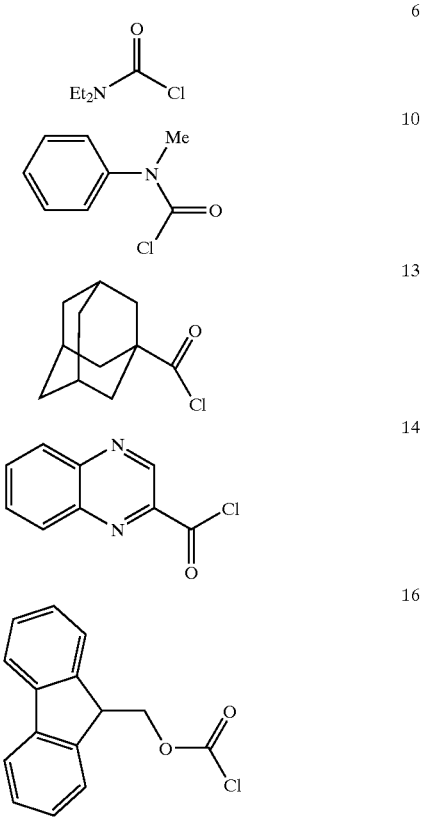

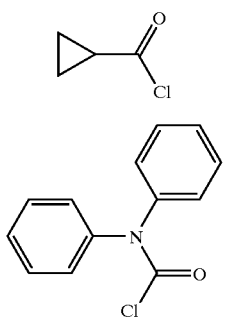

Wherein Cl represents the point of attachment of the capping group.

Attaching the capping group to the targeting compound is achieved by the formation of an amide bond between the terminal carbon molecule of the capping group and the amino group of the amino acid of the targeting compound to which the capping group is attached. The Cl dissociates from the terminal carbon of the capping group upon formation of the amide bond.

Preferred capping groups have an amide group or a carbamate group. The capping group has a functionality that makes the entire compound either an antagonist or only a weak agonist of chemotaxis.

To increase the rate of identification of molecules that are tightly bound to the formylpeptide receptor, but which antagonize the effect of fMLF at that receptor, it is desirable to employ techniques established by one skilled in the art of combinatorial chemistry. In view of the uncertainty associated with the effect of incorporation of a metal into the molecular structures, it is also desirable to incorporate the metal into the molecule before biological testing. Hence mixtures (or libraries) of compounds are produced that contain a metal and these are tested in biological assays using techniques established to one skilled in the art of pharmacology. The inclusion of the metal into the molecule at an early stage avoids uncertainty associated with testing unlabeled molecules in biological assays in order to identify leads, and then incorporating the metal. Hence the molecules tested in the mixture are structurally identical to the final labeled molecule, but are non-radioactive, thereby allowing easier testing. Promising mixtures are identified using these assays and the constituent molecules prepared and re-tested.

Following initial selection of a suitable target molecule, a moderately sized focused library of non-radioactive rhenium compounds is prepared as mixtures of up to 25 compounds. Typically, a large library of rhenium targeting moiety conjugates is delivered as equimolar mixtures of 9–25 compounds in 96 well microtiter plates (1 mg/well) for in vitro testing. These are then tested in the relevant assays and the most promising mixtures are segregated for deconvolution.

Depending on the number of promising molecules, discovered, a second round of testing may then be undertaken using a smaller subset of the rhenium containing molecules together with a second set of biological tests to further reduce the number of molecules. The final iteration will provide a series of discrete compounds as both the rhenium complex and a free chelator ready for labeling with radioactive $^{99m}$technetium which is isostructural to the non-radioactive rhenium isotope used. The potential imaging lead candidates (preferably about 10 compounds) are delivered as pure chelator targeting moiety conjugates for radiolabeling development and in vivo studies. This process provides labeled compounds that are effective for binding a biological target in a rapid and cost effective manner.

The preferred targeting compounds of the present invention correspond to formula II. The preferred targeting compounds have the following formula III when a metal is attached to the chelator:

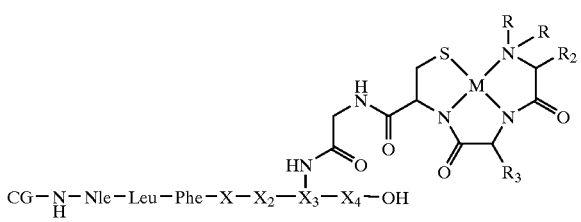

wherein CG is a capping group that makes the compound an antagonist or a weak agonist to chemotaxis; X, X2, X3 and X4 are amino acids selected from natural and unnatural amino acids (SEQ ID NOS: 1–109); X3 being a site of attachment for said chelator; R, and R2 is a linear or branched, saturated or unsaturated $C_{1-6}$ alkyl chain that is optionally interrupted by one or two heteroatoms selected from N, O, and S; and is optionally substituted by at least one group selected form hydroxyl, amino, carboxyl, $C_{1-6}$ alkyl, aryl and C(O)R; R3 is selected from H; alkyl; an alkyl substituted by a group selected from amino, aminoacyl, carboxyl, guaniginyl, hydroxyl, thiol, phenyl, phenolyl, indoly, and imidazolyl; M is a metal.

The most preferred targeting compound have the following formula IV:

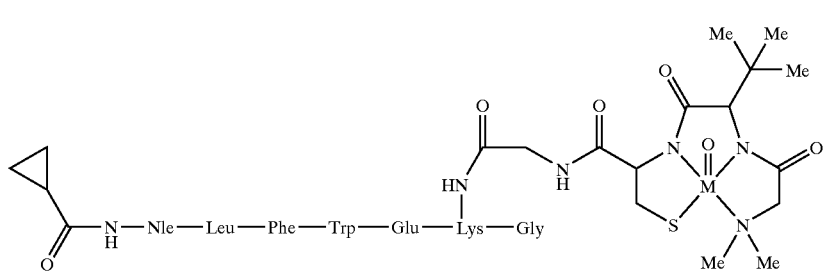

Wherein M is 99m Tc or Re and wherein the peptide sequence NLeu-Leu-Phe-Trp-Glu-Lys-Gly is SEQ. ID No. 1

Methods and Materials

Peptide Synthesis

The effect of N-terminal capping groups on chemotactic peptide function and binding characteristics was investigated by the preparation of the peptide norleucyl-leucyl-phenylalanyl-lysine-COOH with the attachment of several capping groups to the N-terminus as described above.

The various peptide sequences containing varying side chain protecting groups in these examples were synthesized via a solid phase synthesis method on an automated synthesizer using FastMoc chemistry on 1.0 mmol scale. The C-terminus of the peptide was attached to the solid phase via the sasrin linker. Prior to the addition of each amino acid residue (or mixture of acids as described above) to the N-terminus of the peptide chain the FMOC group was removed with 20% piperidine in NMP. Each FMOC amino acid was activated with 0.5M HOBT/HBTU/DMF in the presence of 2.0M DIEA/NMP. After completion of the synthesis the resin was washed with NMP followed by dichloromethane and dried under vacuum for up to 24 hours. Where mixtures of amino acids were employed the three amino acids were added as equimolar mixtures of suitably side chain protected FMOC acid residues in a single coupling step and otherwise treated as a single amino acid residue. Amino capping groups were added as described in example 1.

Synthesis of ReO-Dimethylglycine-t-butyl-glycine-S-Acetamidomethyl-Cysteine-Glycine(ReO-RP455) tetrafluorophenyl ester To ReO-RP455 (60 mg) in 1:1 acetonitrile:water (1 mL) was added tetrafluorophenol (100 mg). The solution was diluted with acetonitrile (2 mL). The pH was adjusted to 2. To the solution was added 1(3-dimethylaminopropyl)-3-ethylcarbodiimide hydrochloride. The reaction was swirled to dissolve and the pH adjusted to 5. The reaction was allowed sit at room temperature for 15 minutes followed by concentrating to a dark oil in vacuo. The product was purified on a Supelco superclean LC-18 column. The column was first washed with a 5% acetonitrile: 95% water solution acidified to pH2 with 3N HCl. The product was eluted in a 50% acetonitrile: 50% water solution acidified to pH2 with 3N HCl. The appropriate pure fractions were identified by silica TLC (t-butanol:water:methanol, 10:3:2, rf: 0.85) followed by $KMnO_4$ staining. The correct fractions were pooled and concentrated in vacuo to a red-brown glass (58 mg).

Synthesis of Libraries of Rhenium-Containing Molecules on Sasrin Resin

Each of the N-terminus capped libraries on sasrin resin (20 mg) was placed in a Biorad disposable column. The Dde epsilon amino group protection on C-terminus Lysine was first removed with three washes of 2% hydrazine in N-methylpyrrolidone (3×1 mL). The resin was thoroughly washed with N-methylpyrrolidone then dichloromethane, and dried in vacuo. To each vessel was added ReO-Dimethylglycine-t-butyl-glycine-S-Acetamidomethyl-CysteineGlycine(ReO-RP455) tetrafluorophenyl ester (10 mg) in ethyl acetate (1 mL). The reactions were capped and shaken 20 hours at room temperature, followed by filtration, washing with copious ethyl acetate, N-methylpyrrolidone, dichloromethane. The red-brown resins were dried in vacuo.

Cleavage of Rhenium-Containing Molecule Mixtures

Each of the ReO libraries were liberated from the supports in 95% TFA: 5% water (1 mL) after 4 hours shaking at mom temperature, followed by filtration. The products were concentrated in vacuo. The residue was redissolved in trifluoroacetic acid (150 uL) and dripped into t-butylmethyl ether (5 mL) to precipitate. Each was centrifuged to a pellet, the solvent decanted and the pellets dried in vacuo. The products were dissolved in water and acetontrile (~5 mL) and lyophilized to pale pink powders.

Preparation of Single Molecules Containing Rhenium

Analysis of the results of the biological testing of the mixtures of rhenium-containing molecules identified some mixtures as having higher binding affinity than others have. The mixture having the highest affinity was chosen for further deconvolution. The molecules were prepared according to the methods used to prepare the mixtures of molecules, with the mixed amino acids being replaced by single amino acids. The rhenium-containing molecules, once cleaved from the resin, were purified by reverse phase HPLC to give pure molecules exhibiting the following physical properties:

ReO-CyclopropylCONH-nleu-leu-phe-trp-glu-lys (dimethylgly-t-butylgly-cys-gly)-gly-OH (wherein the peptide sequence NLeu-Leu-Phe-Trp-Glu-Lys-Gly is SEQ. ID No. 1) HPLC retention time: 22 min; ESMS (1518, M+H), expected 1518

ReO-CyclopropylCONH-nleu-leu-phe-ser-glu-lys (dimethylgly-t-butylgly-cys-gly)-gly-OH (wherein the peptide sequence NLeu-Leu-Phe-Ser-Glu-Lys-Gly is SEQ. ID No. 2) HPLC retention time: 19.8 min; ESMS (1420, M+H), expected 1420

ReO-CyclopropylCONH-nleu-leu-phe-tyr-glu-lys (dimethylgly-t-butylgly-cys-gly)-gly-OH, (wherein the peptide sequence NLeu-Leu-Phe-Tyr-Glu-Lys-Gly is SEQ. ID No. 3) HPLC retention time: 20.1 min ReO-CyclopropylCONH-nleu-leu-phe-trp-his-lys (dimethylgly-t-butylgly-cys-gly)-gly-OH Gly-lys (dimethylgly-t-butylgly-cys-gly)-his-trp-phe-leu-nleu-NHCOcyclopropyl (wherein the peptide sequence NLeu-Leu-Phe-Trp-His-Lys-Gly is SEQ. ID No. 4) HPLC retention time: 21.0 min; ESMS (1528, M+H), expected 1528

ReO-CyclopropylCONH-nleu-leu-phe-ser-his-lys (dimethylgly-t-butylgly-cys-gly)-gly-OH (wherein the peptide sequence NLeu-Leu-Phe-Ser-His-Lys-Gly is SEQ. ID No. 5) HPLC retention time: 19.2 min; ESMS (1515, M+H), expected 1515

ReO-CyclopropylCONH-nleu-leu-phe-tyr-his-lys (dimethylgly-t-butylgly-cys-gly)-gly-OH (wherein the peptide sequence NLeu-Leu-Phe-Tyr-His-Lys-Gly is SEQ. ID No. 6) HPLC retention time: 19.3 min; ESMS (1502, M+H), expected 1502

ReO-CyclopropylCONH-nleu-leu-phe-trp-lys-lys (dimethylgly-t-butylgly-cys-gly)-gly-OH (wherein the peptide sequence NLeu-Leu-Phe-Trp-Lys-Lys-Gly is SEQ. ID No. 7) HPLC retention time: 20.5 min; ESMS (1517, M+H), expected 1517

ReO-CyclopropylCONH-nleu-leu-phe-ser-lys-lys (dimethylgly-t-butylgly-cys-gly)-gly-OH (wherein the peptide sequence NLeu-Leu-Phe-Ser-Lys-Lys-Gly is SEQ. ID No. 8) HPLC retention time: 18.8 min; ESMS (1417, M+H), expected 1417

ReO-CyclopropylCONH-nleu-leu-phe-tyr-lys-lys (dimethylgly-t-butylgly-cys-gly)-gly-OH (wherein the peptide sequence NLeu-Leu-Phe-Tyr-Lys-Lys-Gly is SEQ. ID No. 9) ESMS (1495, M+H), expected 1495

Animals and Reagents.

Sprague-Dawley rats weighing 300–350 g were purchased from Charles River-Bausch & Lomb Laboratories (St.Constant, Quebec). Procedures were in accordance with standard Animal Care Committee protocols. The following compounds were used in this study: fMLF, N-tedbutyloxycarbonylated-methionyl-leucyl-phenylalanine (N-t-BocMLF), cytochalasin B, oyster shell glycogen, polyethylenimine, o-phenylenediamine (OPD), $H_2O_2$, $H_2SO_4$, sodium chloride tablets (Sigma Chemical Corp., St. Louis, Mo.) and $^3$H-fMLF (New England Nuclear, Boston, Mass.). Peptide fMLP analogues, N-formyl-methionyl-leucyl-phenylalanyl-lysine (fMLFK), iso-BocMLFK, N-terminus capping groups 2–4, 6, 7, 10, 12, 13–21 attached to amino acid sequence norleucylleucyl-phenylalanyl-lysine (NleLFK); libraries ReORP552 to 557, deconvolution compounds ReORP553 17-01 to 17–09 and RP553 17-01 were synthesized in-house by Resolution Pharmaceuticals Inc. chemists (Mississauga, ON). fMLF peptide, N-t-BocMLF and fMLF peptide analogues were stored at −20° C. in powder form and were diluted prior to each experiment in 2:1 acetonitrile:$H_2O$. N-terminal capping groups attached to peptide backbone NleLFK were dissolved in DMSO and stored at −20° C. prior to use.

Rat Neutrophil Elicitation and Isolation.

Animals were sacrificed via administration of $CO_2$ 4 hours following peritoneal injection of 10 mL of 0.5% (w/v) oyster glycogen warmed to room temperature. Leukocyte harvesting via peritoneal lavage was performed using 20 mL of Hanks' buffered salt solution (HBSS−) containing 10 mM ethylene-diaminetetra-acetic acid (EDTA) disodium salt followed by a second lavage with 10 mL of HBSS− containing 10 mM EDTA. Exactly the same technique was performed on all rats with washes of the peritoneum prior to aspiration of samples approximating 1 minute. The volume of fluid recovered from each rat was approximately 20–25 mL and bloody lavages visibly containing significant red blood cell (RBC) populations were discarded.

Neutrophils isolated by peritoneal lavage were washed twice with 1 mL of HBSS− (without calcium chloride, magnesium chloride and magnesium sulfate) and centrifuged for ten minutes at 2000 rpms following each wash. PMNs utilized in functional assays were centrifuged at 25° C. while those used in binding assays were centrifuged at 4° C. to prevent internalization. A cold $H_2O$ RBC lysis was then performed with the addition of 9 mL of sterile ice-cold $H_2O$ and 1 mL of phosphate buffered saline (PBS) solution containing 0.1 M phosphate buffer, 0.027 M KCl and 1.37 M NaCl following resuspension of the sample in 1 mL of HBSS−. Centrifugation was subsequently performed for ten minutes at 1600 rpms. White blood cell (WBC) differential stain containing saline, 2% acidic acid and phenol violet dye was used to identify the neutrophil population and trypan blue exclusion was used to determine viability of cells. As previously reported, 98% of leukocytes were neutrophils and approximately 95% of the cells were viable (Chen et al., 1996).

Human Neutrophil Isolation from Whole Blood.

Approximately 30 mL of venous blood was collected from healthy volunteers with 100 units of heparin per mL of blood. Samples were then mixed with 8 mL of 6% dextran solution and incubated at 37° C. for 1 hour for RBC sedimentation. Leukocyte-rich plasma was collected and centrifuged at 1500 rpm for 5 minutes. Cell pellets were resuspended in 35 mL of saline and 10 mL of lymphocyte separation medium was layered over prior to additional centrifugation at 1200 rpm for 30 minutes. Sedimented cells were washed once with 35 mL of saline and RBCs were lysed by resuspension in 1.8 mL of sterile $H_2O$ for 15 seconds. Isotonicity was restored with the addition of 0.2 mL of 10×HBSS− followed by the addition of 35 mL of saline. Centrifugation at 1500 rpm for 5 minutes was then performed. Following final washing of the PMN pellet with 35 mL of saline, cell viability was determined via trypan blue exclusion and cell number was determined.

Neutrophil fMLP Receptor Binding Assays.

$K_D$ values were determined with fMLP saturation binding experiments using $2.5 \times 10^5$ PMNs per well suspended in a final volume of 150 uL of FMLP, $^3$H-fMLP and/or HBSS+ in polypropylene 96-well plates. Each condition was performed in quadruplicate and non-specific binding was assessed in the presence of PMNs, 10 uM fMLP and $^3$H-fMLP in the range of 1 nM to 150 nM. Total binding was evaluated following the addition of $^3$H-fMLP in the concentration range of 1 nM to 150 nM for development of a saturation curve. The total amount of activity added to each sample was determined from counts per minute (cpms) obtained from a sample containing 50 nM $H^3$-fMLF. In all binding assays, specific binding was expressed in fmol and defined as difference between total binding and non-specific binding.

Competition binding assays for N-terminal capping groups and Re-libraries were conducted with 6 nM $^3$H-fMLP in addition to the unlabelled competing analogue added at 1.0 uM and 10 uM to each well. For $IC_{50}$ value determination, the concentration of library mixture ReORP553 17 deconvolution compounds, ranged from $10^{-12}$M to $10^{-3}$M in the presence of 6 nM $^3$H-fMLF. Total binding in the competition assays was assessed in the presence of $1.0 \times 10^6$ PMNs per sample while non-specific binding was determined in the absence of cells. Each condition was performed in quadruplicate. Total activity added to each sample was determined from cpms obtained from a sample containing 6 nM $^3$H-fMLF. Data was expressed as specific binding in fmols and converted to percent of total $^3$H-fMLF binding (% control).

After a 1 hour incubation period at 4° C., the samples were harvested with the Tomtec Mach III Cell Harvester by vacuum aspiration onto 1.5 um pore size Skatron glass-fibre filter mats pre-treated with 0.1% polyethylenimine (w/v) for approximately 24 hours. Sample wells received three consecutive 12 second washes with 0.9% saline solution and 5 mL of liquid scintillation fluid was added to collected filters. Filters were counted for 2 minutes in the Beckman β-counter following exposure to scintillation fluid for 15 hours. Data was expressed in terms of specific binding in fmols converted to percent of total $^3$H-fMLF binding (% control).

Measurement of Myeloperoxidase Release.

$0.5 \times 10^6$ PMNs per sample were incubated in 96well Millipore Multiscreen 0.65 um filter plates. In a final volume of 150 uL, 50 uL of the respective fMLP analogues (10 uM. to 1 pM) and/or FMLP (10 uM to 1.0 uM) were incubated with isolated PMNs pre-treated with cytochalasin B (5 ug/mL) for 10 minutes. Following a 30 minute incubation period at room temperature, the supernatant was collected into a 96-well polypropylene plate with the Millipore vacuum apparatus. A stock solution of o-phenylenediamine (OPD) was made to contain 2.5 mg of OPD, 5 ul of $H_2O_2$ and 10 mL HBSS+ and supernatant samples were subsequently incubated with 50 uL of OPD solution. The reaction was stopped after 2 minutes by the addition of 2.5M $H_2SO_4$. Photometric analysis was performed with the Thermomax Microplate Reader with optical density ($O.D._{490}$) values being read at a wavelength of 490 nm. Absorbance was measured against a blank containing 150 ul of HBSS+ which was subtracted from wells containing cells and the various treatments. MPO release was expressed as a percentage of the total release of myeloperoxidase in control wells containing cells±fMLF.

Radiolabeling of RP553 17-01

RP553 17-01 (200 ug; 0.144 umoles) was dissolved in 100 ul saline and 100 ul acetonitrile. Tin (II) chloride (40 ug) and sodium gluconate (1.3 mg) was added to the peptide solution followed by Na[$^{99}$TcO4] (10 mCi). The reaction was carried out for one hour at room temperature. The reaction was analyzed using high performance liquid chromatography (HPLC) and the product was purified under a step-gradient condition.

Data Analysis

The curve-fitting program Prism was used to calculate $K_D$, $IC_{50}$ and $EC_{50}$ values by fitting data to the one-site binding equations A, B and C respectively.

A. Equation: One site binding (hyperbola)

$$Y = B\max \cdot X/(K_D + X)$$

B. Equation: One site competition $$Y = \text{Bottom} + (\text{Top} - \text{Bottom})/(1 + 10^{(X-\log IC50)});$$ with $x = \log$ (concentration) and $y = $ binding C. Equation: Sigmoidal dose-response (variable slope)

$$Y = \text{Bottom} + (\text{Top} - \text{Bottom})/(1 + 10^{((\log EC50 - X) \cdot \text{Hill Slope})})$$

The goodness of fit for data to the above equations was determined by the correlation coefficient (with r=1 being a perfect fit) and 95% confidence intervals were calculated for $IC_{50}$ and $EC_{50}$ values. Additionally, Graph fit software was used to perform Scatchard analysis of saturation binding data and to confirm $K_D$ and Bmax values generated by Prism software.

Individual experiments (denoted by n values) were performed in quadruplicate to account for intra-assay variability. Results are expressed as means±S.E.M. unless otherwise indicated. Statistical significance among multiple groups was evaluated with a one way analysis of variance while a student's t-test was used to evaluate significance between sample treatments. A p value of <0.05 was considered significant Experimental Results Library Design Based on capping group data, a combination of parallel synthesis and split and mix technologies was used to prepare a combinatorial library of 324 Re-peptides. Specifically the library was composed of 36 mixtures containing equimolar quantities of 9 different compounds for analysis in binding studies based on the following peptide sequence (wherein the peptide sequence nLeu-Leu-Phe-Xaa-Xaa-Lys-Gly is Seq. ID No. 10):

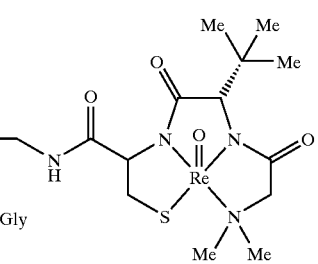

Where A, B, C, D, E, F are natural amino acids and the capping groups (CG) are selected from those above. The following table indicates the amino acids and capping groups used in individual libraries.

TABLE 1

Amino acid substitutions and N-terminal capping groups for Re-Library Mixtures

| RP# | Mixture A, B, C | Mixture D, E, F | Capping Group |
|---|---|---|---|
| 552-6 | Phe, Asp, Leu | Trp, Ser, Tyr | N,N-diethycarbamyl |
| 552-10 | Phe, Asp, Leu | Trp, Ser, Tyr | N-phenyl,N-methylcarbamyl |
| 552-13 | Phe, Asp, Leu | Trp, Ser, Tyr | Adamantylcarbonyl |
| 552-16 | Phe, Asp, Leu | Trp, Ser, Tyr | Fluorenylmethylcarbonyl |
| 552-17 | Phe, Asp, Leu | Trp, Ser, Tyr | Cyclopropylcarbonyl |

TABLE 1-continued

Amino acid substitutions and N-terminal capping groups for Re-Library Mixtures

| RP# | Mixture A, B, C | Mixture D, E, F | Capping Group |
|---|---|---|---|
| 552-18 | Phe, Asp, Leu | Trp, Ser, Tyr | N,N-diphenylcarbamyl |
| 553-6 | Glu, His, Lys | Trp, Ser, Tyr | N,N-diethycarbamyl |
| 553-10 | Glu, His, Lys | Trp, Ser, Tyr | N-phenyl,N-methylcarbamyl |
| 553-13 | Glu, His, Lys | Trp, Ser, Tyr | Adamantylcarbonyl |
| 553-16 | Glu, His, Lys | Trp, Ser, Tyr | Fluorenylmethylcarbonyl |
| 553-17 | Glu, His, Lys | Trp, Ser, Tyr | Cyclopropylcarbonyl |
| 553-18 | Glu, His, Lys | Trp, Ser, Tyr | N,N-diphenylcarbamyl |
| 554-6 | Asn, Arg, Val | Glu, His, Lys | N,N-diethycarbamyl |
| 554-10 | Asn, Arg, Val | Glu, His, Lys | N-phenyl,N-methylcarbamyl |
| 554-13 | Asn, Arg, Val | Glu, His, Lys | Adamantylcarbonyl |
| 554-16 | Asn, Arg, Val | Glu, His, Lys | Fluorenylmethylcarbonyl |
| 554-17 | Asn, Arg, Val | Glu, His, Lys | Cyclopropylcarbonyl |
| 554-18 | Asn, Arg, Val | Glu, His, Lys | N,N-diphenylcarbamyl |
| 555-6 | Phe, Asp, Leu | Asn, Arg, Val | N,N-diethycarbamyl |
| 555-10 | Phe, Asp, Leu | Asn, Arg, Val | N-phenyl,N-methylcarbamyl |
| 555-13 | Phe, Asp, Leu | Asn, Arg, Val | Adamantylcarbonyl |
| 555-16 | Phe, Asp, Leu | Asn, Arg, Val | Fluorenylmethylcarbonyl |
| 555-17 | Phe, Asp, Leu | Asn, Arg, Val | Cyclopropylcarbonyl |
| 555-18 | Phe, Asp, Leu | Asn, Arg, Val | N,N-diphenylcarbamyl |
| 556-6 | Trp, Ser, Tyr | Asn, Arg, Val | N,N-diethycarbamyl |
| 556-10 | Trp, Ser, Tyr | Asn, Arg, Val | N-phenyl,N-methylcarbamyl |
| 556-13 | Trp, Ser, Tyr | Asn, Arg, Val | Adamantylcarbonyl |
| 556-16 | Trp, Ser, Tyr | Asn, Arg, Val | Fluorenylmethylcarbonyl |
| 556-17 | Trp, Ser, Tyr | Asn, Arg, Val | Cyclopropylcarbonyl |
| 556-18 | Trp, Ser, Tyr | Asn, Arg, Val | N,N-diphenylcarbamyl |
| 557-6 | Ile, Gln, Thr | Asn, Arg, Val | N,N-diethycarbamyl |
| 557-10 | Ile, Gln, Thr | Asn, Arg, Val | N-phenyl,N-methylcarbamyl |
| 557-13 | Ile, Gln, Thr | Asn, Arg, Val | Adamantylcarbonyl |
| 557-16 | Ile, Gln, Thr | Asn, Arg, Val | Fluorenylmethylcarbonyl |
| 557-17 | Ile, Gln, Thr | Asn, Arg, Val | Cyclopropylcarbonyl |
| 557-18 | Ile, Gln, Thr | Asn, Arg, Val | N,N-diphenylcarbamyl |

Competition Binding of Rhenium-Libraries

Potential capping group modifications identified as antagonists (6, 10, 13, 16, 17) or agonists with reduced activity (18) in functional screens as well as in preliminary binding assays were implemented into the library design. The application of combinatorial chemistry allowed for high-throughput screening of a library of 36 mixtures consisting of equimolar concentrations of 9 compounds all of which were complexed to Re. Each library (labeled 552 to 557) varied in the specific amino acids incorporated at position 4 and 5 from the N-terminus. Furthermore, additional variation within a single library (e.g. 552) was introduced with the addition of varied N-terminal capping groups.

Figure 1B:
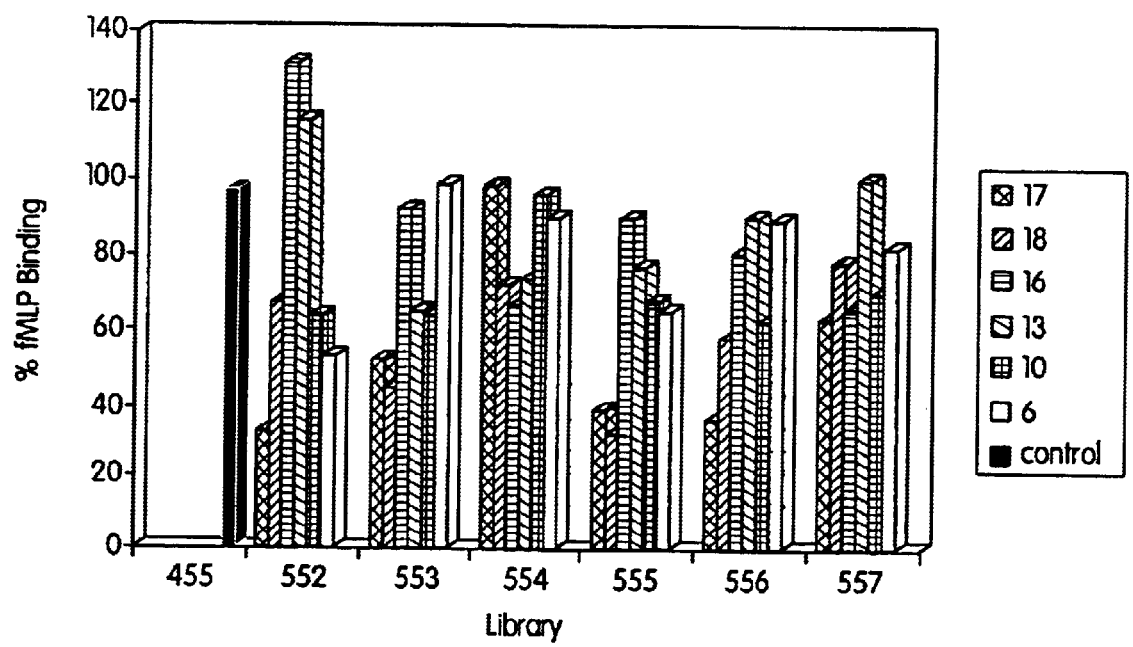
FIG. 1B represents competition binding of library mixtures administered at 1.0 uM concentrations.
Figure 2:
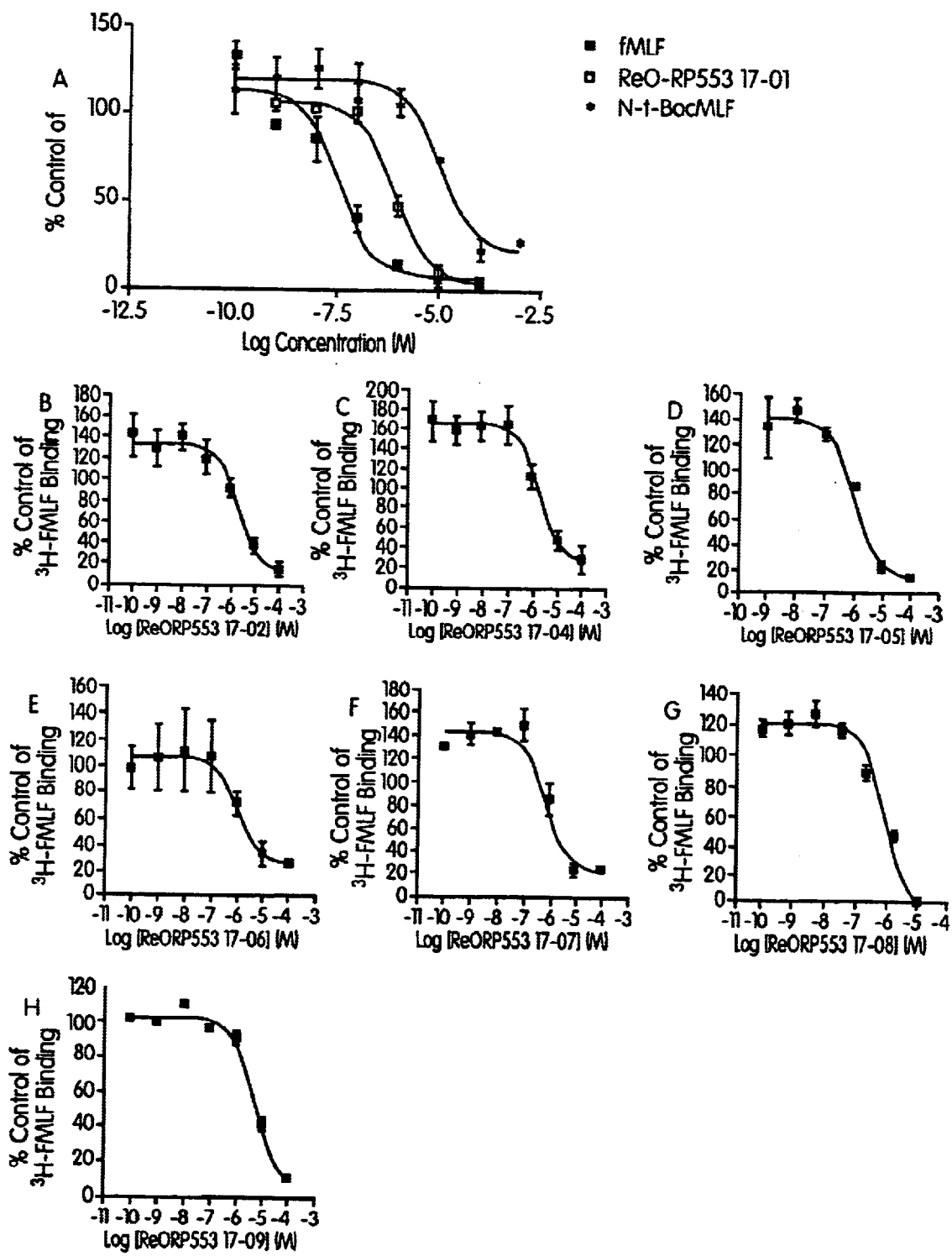
FIG. 2 shows competition-binding curves of library ReORP553 deconvolution compounds with 6 nM $^3$H-fMLF. Fit of curves to one-site competition function with Prism software is indicated for a correlation coefficient ≧0.98 for all graphs. ReORP553 17-01 exhibited the greatest binding affinity and the receptor binding curve in relation to control compounds fMLF and N-t-BocMLF which is represented in graph A.

Competition binding data of libraries at 1.0 uM and 10 uM with 6 nM $^3$H-fMLF indicate dose-dependent inhibition of $^3$H-fMLF binding in all cases as shown in FIGS. 1A and 1B respectively). It should be noted that the control compound (designated 455 on figure 1A and 1B) represents binding by Re-metal complexed to the chelator (Dimethylgly-t-Butylgly-cys-gly-). This negative control did not inhibit ³H-fMLF binding to any significant degree. Several mixtures (ReORP552-17, ReORP553-17, ReORP555-17, ReORP556-17, ReORP555-18, etc.) exhibit significant displacement of ³H-fMLF whereas other mixtures exhibit relatively weak binding properties (ReORPS554-17, ReORP554-10, ReORP557-13, etc.) This variation was used to decide which mixtures require deconvolution into 9 separate compounds for further testing.

Deconvolution of Mixture ReORP553 17

Library mixture ReORP553 17 showing the highest binding affinity (lowest fMLP remaining) in competition binding assays (RP553-17) was selected and the constituent single peptides were prepared and isolated as pure compounds. The following is a list of the corresponding amino acid sequences for individual Re-peptides:

RP533-17-01
ReO-CyclopropylCONH-nleu-leu-phe-trp-glu-lys (dimethylgly-t-butylgly-cys-gly)-gly-OH (wherein the peptide sequence NLeu-Leu-Phe-Trp-Glu-Lys-Gly is SEQ. ID No. 1) HPLC retention time:22 min; ESMS (1518, M+H), expected 1518

RP553-17-02
ReO-CyclopropylCONH-nleu-leu-phe-ser-glu-tys (dimethylgly-t-butylgly-cys-gly)-gly-OH (wherein the peptide sequence NLeu-Leu-Phe-Ser-Glu-Lys-Gly is SEQ. ID No. 2) HPLC retention time: 19.8 min; ESMS (1420, M+H), expected 1420

RP553- 17-03
ReO-CyclopropylCONH-nleu-leu-phe-tyr-glu-lys (dimethylgly-t-butylgly-cys-gly)-gly-OH (wherein the peptide sequence NLeu-Leu-Phe-Tyr-Glu-Lys-Gly is SEQ. ID No. 3) HPLC retention time: 20.1 min RP553-17-04
ReO-CyclopropylCONH-nleu-leu-phe-trp-his-lys (dimethylgly-t-butylgly-cys-gly)-gly-OH Gly-lys (dimethylgly-t-butylgly-cys-gly)-his-trp-phe-leu-nleu-NHCOcyclopropyl (wherein the peptide sequence NLeu-Leu-Phe-Trp-His-Lys-Gly is SEQ. ID No. 4) HPLC retention time: 21.0 min; ESMS (1528, M+H), expected 1528

RP553-17-05
ReO-CyclopropylCONH-nleu-leu-phe-ser-his-lys (dimethylgly-t-butylgly-cys-gly)-gly-OH, (wherein the peptide sequence NLeu-Leu-Phe-Ser-His-Lys-Gly is SEQ. ID No. 5) HPLC retention time: 19.2 min; ESMS (1515, M+H), expected 1515

RP553-17-06
ReO-CyclopropylCONH-nleu-leu-phe-tyr-his-lys (dimethylgly-t-butylgly-cys-gly)-gly-OH (wherein the peptide sequence NLeu-Leu-Phe-Tyr-His-Lys-Gly is SEQ. ID No. 6) HPLC retention time: 19.3 min; ESMS (1502, M+H), expected 1502

RP553-17-07
ReO-CyclopropylCONH-nleu-leu-phe-trp-lys-lys (dimethylgly-t-butylgly-cys-gly) -gly-OH (wherein the peptide sequence NLeu-Leu-Phe-Trp-Lys-Lys-Gly is SEQ. ID No. 7) HPLC retention time: 20.5 min; ESMS (1517, M+H), expected 1517

RP553-17-08
ReO-CyclopropylCONH-nleu-leu-phe-ser-lys-lys (dimethylgly-t-butylglycys-gly)-gly-OH (wherein the peptide sequence NLeu-Leu-Phe-Ser-Lys-Lys-Gly is SEQ. ID No. 8) HPLC retention time: 18.8 min; ESMS (1417, M+H), expected 1417

RP553-17-09
ReO-CyclopropylCONH-nleu-leu-phe-tyr-lys-lys (dimethylgly-t-butylgly-cys-gly)-gly-OH (wherein the peptide sequence NLeu-Leu-Phe-Tyr-Lys-Lys-Gly is SEQ. ID No. 9) ESMS (1495, M+H), expected 1495

Competition Binding of Mixture ReORP553 Deconvolution Compounds

Although several Re-libraries exhibited significant displacement of 6 nM ³H-fMLF, library ReORP553 17-01 was chosen for deconvolution due to high-degree of ³H-fMLF displacement exhibited at 10 uM. Deconvolution compound synthesis yielded eight ReO-peptides exhibiting purity greater than 80%. Complexation of rhenium to the final ninth peptide (ReORP553 17-03) of this mixture could not be successfully synthesized with due to relatively low yield so it is not indicated in the deconvolution results.

All nine N-terminal cyclopropanecarbonyl-modified peptides with varying amino acid sequences exhibited dose-dependent competition in the receptor binding assays. For comparative measures, fMLF and N-t-BocMLF were evaluated as representative agonist and antagonist standards respectively. Competition binding curves for deconvolution compounds are exhibited in FIGS. 1A–H and respective IC50 values derived from these curves are summarized in Table V. Although none of the Re-peptides exhibited greater binding affinity than fMLF, all of them were at least 1.5-fold more potent than N-t-BocMLF. Furthermore, ReORP553 17-01 exhibited the highest binding affinity which was approximately 12-fold greater than known antagonist N-t-BocMLF but 15-fold less than fMLF. The structure and corresponding amino acid sequence of ReORP553 17-01 is as follows (wherein the peptide sequence NLeu-Leu-Phe-Trp-Glu-Lys-Gly is SEQ. ID No. 1):

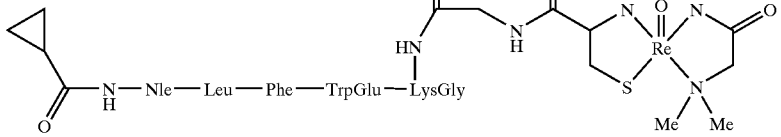

TABLE 2

Rat FPR Binding for deconvolution compounds of library ReORP553 17

| Deconvolution Compound | Receptor Binding (IC$_{50}$, uM) | n value |
| --- | --- | --- |
| fMLF | 0.05 (0.008 to 0.27) | 3 |
| N-t-BocMLF | 9.3 (4.21 to 20.57) | 4 |

TABLE 2-continued

Rat FPR Binding for deconvolution compounds of library ReORP553 17

| Deconvolution Compound | Receptor Binding (IC$_{50}$, uM) | n value |
|---|---|---|
| ReORP553 17-01 | 0.73 (0.60 to 0.88) | 3 |
| ReORP553 17-02 | 2.31 (1.41 to 3.79) | 3 |
| ReORP553 17-04 | 1.77 (1.30 to 2.42) | 3 |
| ReORP553 17-05 | 1.01 (0.53 to 1.93) | 3 |
| ReORP553 17-06 | 1.22 (0.62 to 2.4) | 2 |
| ReORP553 17-07 | 0.76 (0.19 to 3.0) | 2 |
| ReORP553 17-08 | 4.95 (1.78 to 13.71) | 2* |
| ReORP553 17-09 | 5.93 (2.96 to 11.91) | 1* |

Binding of ReORP553 17-01 to Human Neutrophils

Figure 3:
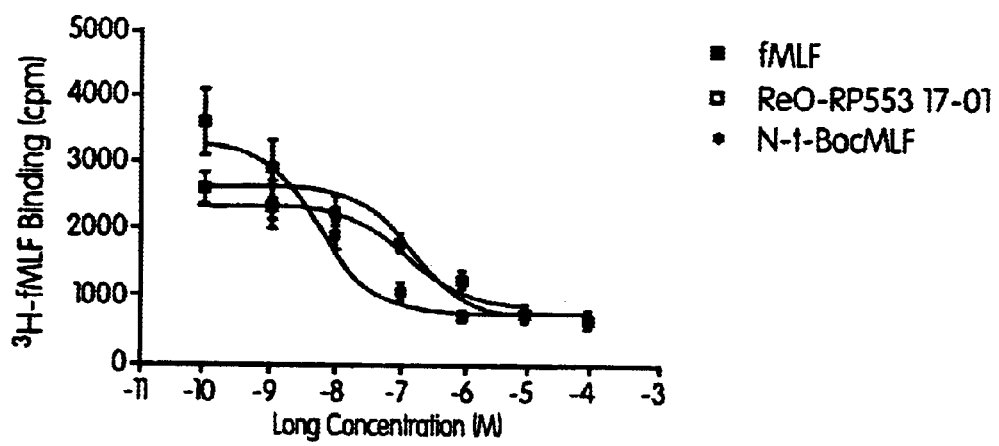
FIG. 3 is a binding curve showing competition binding of ReORP553 17-01 with 6 nM $^3$H-fMLF to human neutrophils. Fit of curves to one-site competition function with Prism software indicated a correlation coefficient >0.97 for all binding curves. ReORP553 17-01 exhibited a binding affinity which is similar to N-t-BocMLF and less than fMLF (n=1, performed in replicates of 3)

Competition binding curves of ReORP553 17-01, fLMF and N-t-BocMLF to human neutrophils are shown in FIG. 3. Respective IC$_{50}$ values are shown in Table 3. While fMLF exhibits the lowest IC$_{50}$ value, values for ReORP553 17-01 and N-t-Boc indicate similar binding affinities.

TABLE 3

Human FPR Binding of ReORP553 17-01

| Compound | IC$_{50}$ Value (uM) |
|---|---|
| fMLF | 0.005 (0.0009 to 0.03) |
| ReORP553 17-01 | 0.14 (0.008 to 2.4) |
| N-t-BocMLF | 0.18 (0.03 to 1.04) |

Data is expressed as IC$_{50}$ values (with 95% confidence intervals) (n = 1, performed in triplicate) See FIG. 7 for associated receptor binding curves.

Effect of ReORP553 17-01 on Myeloperoxidase Release from Human Neutrophils

Figure 4:
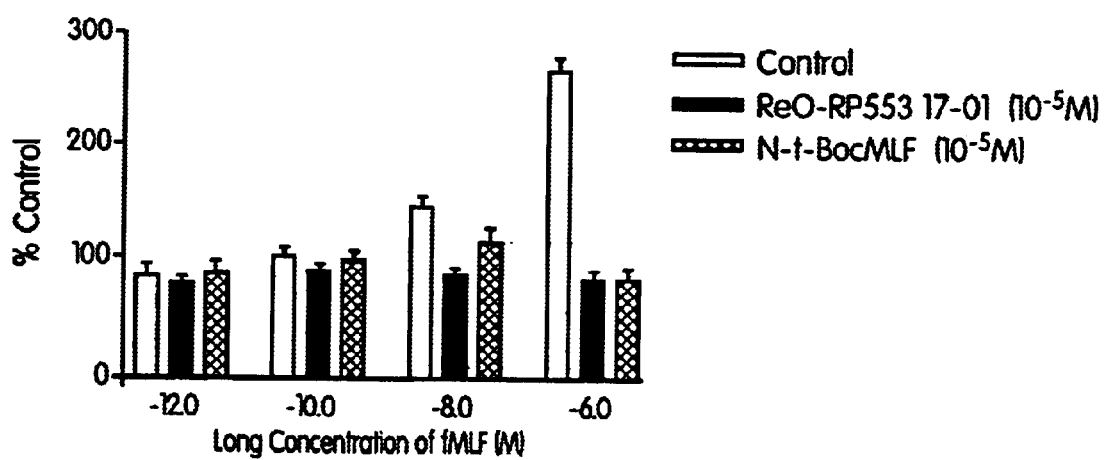
FIG. 4 Is a bar graph showing the effect of ReORP553 17-01 on MPO release in human neutrophils stimulated with varying concentrations of fMLF. Significant inhibition of MPO release is observed by 10 uM ReORP553 17-01 at fMLF concentrations of $10^{-8}$M and $10^{-6}$M. Data is expressed as percent of control absorbance±S.E.M. (n=1, performed in replicates of 4) This effect is comparable to that of N-t-BocMLF, a known antagonist

ReORP553 17-01 significantly inhibited the release of MPO in human neutrophils stimulated with fMLF at concentrations of $10^{-8}$M and $10^{-6}$M (p<0.05) (FIG. 4). Although not shown on FIG. 4, data pertaining to administration of $10^{-14}$M fMLF coincided with data for $10^{-12}$M fMLF in that there was no significant increase in MPO release for any of the treatments. Specifically, ReORP553 17-01 administered at a concentration as high as 10 uM did not stimulate MPO release that indicates that it may be an antagonist. Known antagonist N-t-BocMLF was used as an internal standard and correspondingly inhibited MPO release from fMLF stimulated cells and did not induce release at lower concentrations of fMLF.

Radiolabelling of RP553 17-01 with T chnetium-99m

Figure 5:
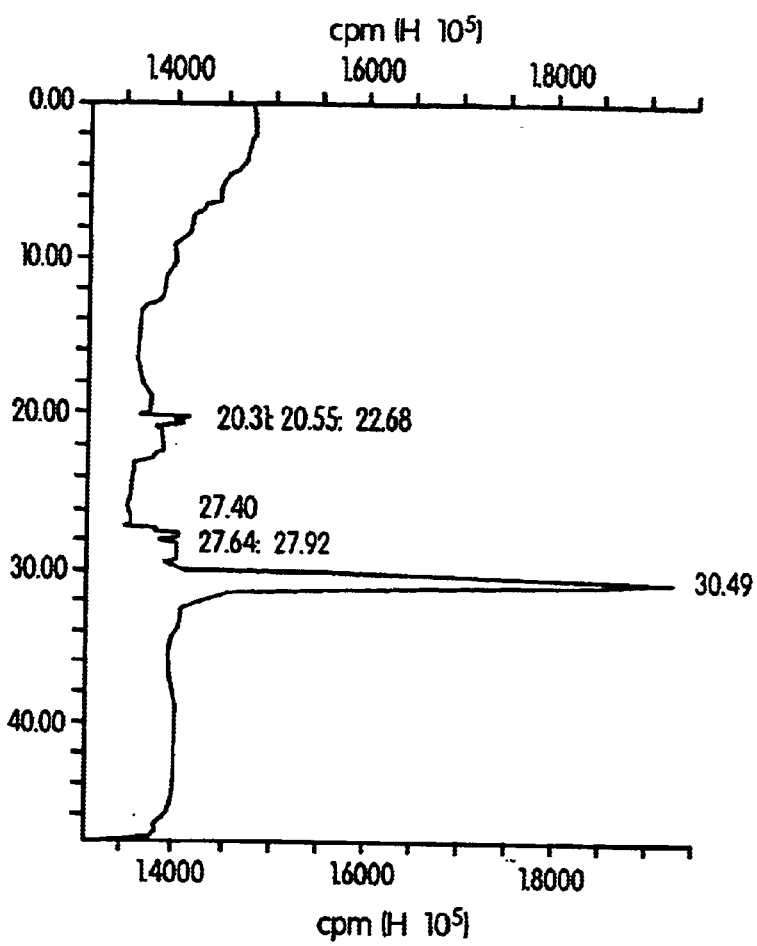
FIG. 5 is a plot showing HPLC purified Tc99m-RP553 17-01 labeling. RP553 17-01 was radiolabeled with 99m sodium pertechnetate under RP553 17-01 (200 ug, 0.144 umoles) was dissolved in 100 ul saline and 100 ul acetonitrile. Tin (II) chloride (40 ug) and sodium gluconate (1.3 mg) were added to the peptide solution followed by Na[$^{99}$TcO$_4$] (10 mCi). The solution was carried out for 1 hour at room temperature. The reaction was analyzed using HPLC and the product was purified under a step-gradient condition. The radiochemical purity of the HPLC purified Tc-99m-RP553 17-01 was >90% as shown in the trace.
Figure 6A:
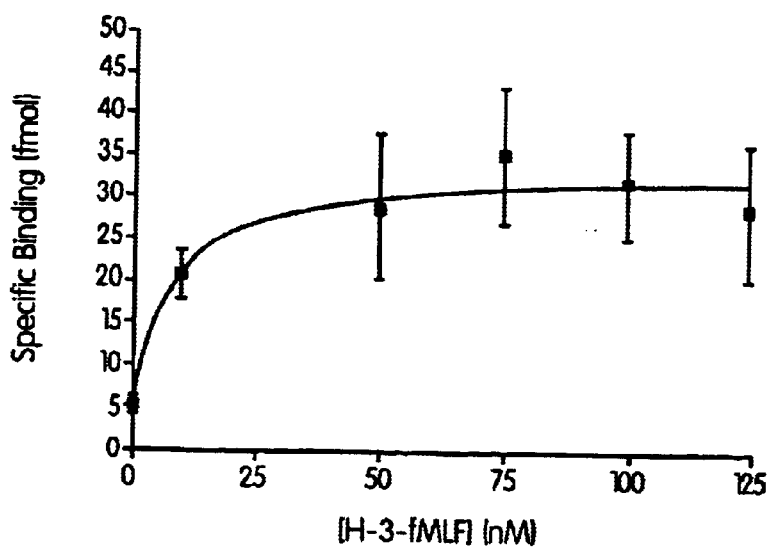
FIG. 6 is a plot showing binding of f-Met-Leu-[3H]Phe to elicited rat peritoneal neutrophils. Neutrophils (0.25× $10^6$–1.0×$10^6$ cells) were incubated at 4° C. for 1 hour with varying concentrations of f-Met-Leu-[³H]Phe. For FIG. 6A the data represents specific binding (total minus nonspecific binding in the presence of excess nonradiolabeled fMLF) (r=0.95). For FIG. 6B the data represents Scatchard transformation of the binding isotherm indicates binding to a single receptor population with a slope of −0.16±0.02 and an x-intercept of approximately 34±0.5 (r=−0.97; n=3 performed in quadruplicate)
Figure 6B:
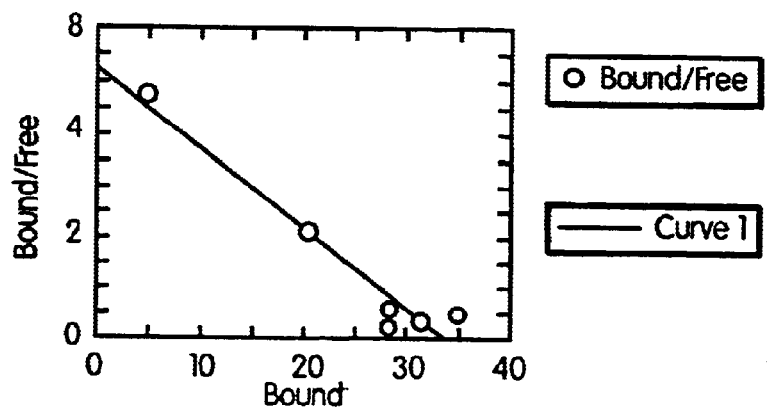

RP553 17-01 was successfully radiolabeled to yield $^{99m}$Tc-RP553 17-01 with >90% radiochemical purity (see FIG. 5). Saturation and Scatchard Analysis of Neutrophil fMLF Receptor Binding Specific binding of [$^3$H]fMLF to peritoneal rat neutrophils was characterized with total [$^3$H]-fMLF concentrations ranging from 1 to 125 nM in the presence and absence of an excess of cold fMLF (FIG. 6A). Analysis of the saturation binding data by Prism software indicated a K$_D$ value of 6.1±2.3 nM and 4.0±0.9×10$^4$ binding sites expressed per cell (n=3) (Table 4). Scatchard analysis (FIG. 6B) suggested the presence of a single class of binding sites (r =−0.97) and confirmed analysis with Prism software with a corresponding K$_D$ value of 6.4±0.02 nM and 4.1±0.06×10$^4$ binding sites per cell.

TABLE 4 fMLF receptor binding on rat neutrophils

| | Binding Sites/Cell | K$_D$ (nM) | n |
|---|---|---|---|
| Control | 4.0 ± 0.9 × 10$^4$ | 6.1 ± 2.3 | 3 |

B$_{max}$ values used to estimate binding sites per cell and the K$_D$ values were derived from one-site binding equation in Prism software. Scatchcard analysis confirmed these results with a K$_D$ of 6.4 ± 0.02 nM and a 4.1 ± 0.06 binding sites per cell. (values expressed as mean ± S.E.M.; n = 3 performed in quadruplicate).

Dose-Response of Myeloperoxidase Release by fMLF and fMLFK

Figure 7A:
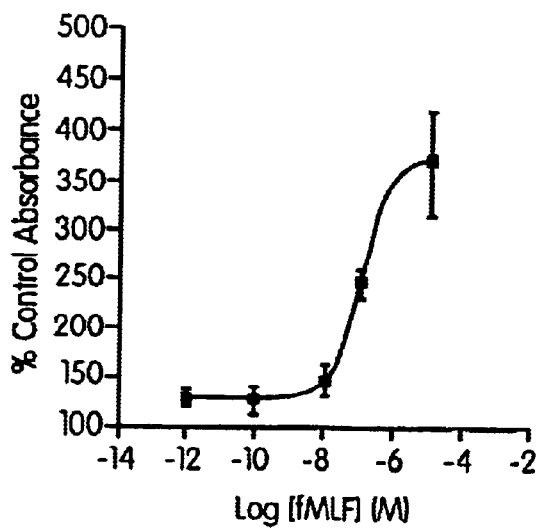
FIG. 7 is a plot that shows the release of MPO by elicited rat peritoneal neutrophils. Dose-dependent release of myeloperoxidase was exhibited by fMLF in FIG. 7A and fMLFK in FIG. 7B. Agonist response is expressed as % of the O.D.$_{490}$ value attained in control wells lacking stimulation and error bars represent S.E.M. values (n=3, performed in quadruplicate; r=0.99)
Figure 7B:
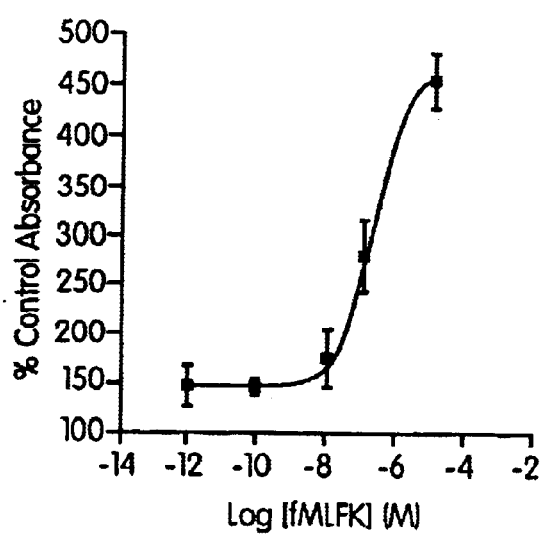

Photometric measurement of myeloperoxidase release from elicited rat PMNs in response to known agonists fMLF and fMLFK indicated a dose-dependent response (FIG. 7A and 7B respectively). EC$_{50}$ values (with 95% confidence intervals) of 0.11 (0.04 to 0.28) uM and 0.14 (0.13 to 0.16) uM for fMLF and fMLFK respectively did not indicate significant differences in agonist potency (p >0.05).

3.3 Effect of fMLF Amine Capping Groups on Myeloperoxidase Release

Several N-terminal capping groups attached to the amino acid backbone NleLFK, were assessed in functional assays to determine agonist or antagonist activity in terms of MPO release. Dose-dependent increases in MPO release were observed with peptides modified with 3-but-1-enoxycarbonyl, 2-acetamido-5-thiazolesulfonyl, 2-quinoxazoyl and trans-cinnamoyl groups indicating agonist activity (Table 5). Although N-terminal modification of the peptide backbone with N,N-diphenylcarbamoyl did not cause a dose-dependent increase in MPO release, the resultant stimulation at the 10 uM concentration was still significant (p<0.05). It should be noted that these compounds were not as potent in stimulating MPO release as the agonist standards fMLF and fMLFK at 1 uM and 10 uM concentrations (See FIG. 7).

TABLE 5

Chemical identification and functional data of amine capping groups displaying agonist function in relation to control values

| Capping Group # | Chemical Identification | % Control (1 uM) | n | P | % Control (10 uM) | N | p |
|---|---|---|---|---|---|---|---|
| 7 | 3-but-1-enoxycarbonyl | 133.8 ± 13.3 | 2 | <0.05 | 229.3 ± 13.3 | 2 | <0.05 |
| 12 | 2-acetamido-5-thiazolesulfonyl | 117.5 ± 7.8 | 2 | >0.05 | 175.5 ± 12.0 | 2 | <0.05 |

TABLE 5-continued

Chemical identification and functional data of amine capping groups displaying agonist function in relation to control values

| Capping Group # | Chemical Identification | % Control (1 uM) | n | P | % Control (10 uM) | N | p |
|---|---|---|---|---|---|---|---|
| 14 | 2-quinoxazoyl | 117.2 ± 18.6 | 2 | >0.05 | 129.8 ± 6.0 | 2 | <0.05 |
| 15 | trans-cinnamoyl | 133.1 ± 10.3 | 2 | <0.05 | 195.8 ± 14.3 | 2 | <0.05 |
| 18 | N,N-diphenylcarbamoyl | 142.7 ± 8.8 | 2 | <0.05 | 125.2 ± 1.5 | 2 | >0.05 |

Control wells consisted of PMNs without any additional ligand present while amine capping groups were administered at 1 uM and 10 uM concentrations. Data is expressed as % control ± S.E.M. and n values represent samples performed in quadruplicate.

Table 6 displays functional data pertaining to amine capping group modifications which did not significantly increase the degree of MPO release in relation to unstimulated PMNs. Specifically, the lack of PMN stimulation exhibited by 2-methoxyacetyl (2), furoyl (3), phenylthioacetyl (4), N,N-diethylcarbamoyl (6) and cyclopropylcarbonyl (17) -NleLFK peptides suggest these modifications result in non-binding or possibly antagonist ligands. However, competition binding assays (FIG. 8) with N,N-diethylcarbamoyl-NleLFK and cyclopropylcarbonyl indicate that these ligands inhibit $^3$H-fMLF binding and are therefore more likely antagonists. Antagonist activity was also observed with N-phenyl-N-methylcarbamoyl(10), adamantanecarbonyl (13) and fluorenylmethylcarbonyl(16) capping groups which significantly decreased basal levels of MPO release resulting from the PMN elicitation process. It should be noted that the degree of MPO release in unstimulated cells was not significantly different from PMNs exposed to known antagonists isoBOC-MLFK and N-t-BocMLFK at concentrations of 1.0 uM and 10 uM.

TABLE 6

Chemical identification and functional data of fMLF amine capping groups which displayed non-binding or antagonist characteristics relative to control values

| Capping Group # | Chemical Identification | % Control (1 uM) | N | P | % Control (10 uM) | n | p |
|---|---|---|---|---|---|---|---|
| 2 | 2-methoxyacetyl | 95.0 ± 15.7 | 2 | >0.05 | 97.1 ± 37.1 | 2 | >0.05 |
| 3 | Furoyl | 93.0 ± 9.0 | 3 | >0.05 | 102.5 ± 9.0 | 3 | >0.05 |
| 4 | Phenylthioacetyl | 138.7 ± 28.6 | 2 | >0.05 | 119.7 ± 20.3 | 2 | >0.05 |
| 6 | N,N-diethylcarbamoyl | 113.8 ± 14.3 | 3 | >0.05 | 109.6 ± 3.3 | 3 | >0.05 |
| 10 | N-phenyl-N-methylcarbamoyl | 94.7 ± 20.4 | 2 | >0.05 | 68.0 ± 17.4 | 2 | <0.05 |
| 13 | Adamantylcarbonyl | 70.5 ± 14.9 | 2 | <0.05 | 71.7 ± 11.2 | 2 | <0.05 |
| 16 | Fluorenylmethylcarbonyl | 84.1 ± 27.6 | 2 | >0.05 | 59.9 ± 19.0 | 2 | <0.05 |
| 17 | Cyclopropylcarbonyl | 108.0 ± 14.5 | 3 | >0.05 | 91.8 ± 16.3 | 3 | >0.05 |
|  | N-t-BocMLFK | 89.8 ± 32.5 | 2 | >0.05 | 86.7 ± 31.1 | 2 | >0.05 |
|  | iso-BocMLFK | 99.6 ± 16.5 | 2 | >0.05 | 94.7 ± 20.2 | 2 | >0.05 |

Control wells consisted of PMNs without any additional ligand while test compounds were administered at 1 uM and 10 uM concentrations. Data is expressed as % control ± S.E.M. and n values represent samples performed in quadruplicate.

In addition to decreasing basal levels of MPO release (Table 6), capping groups 10, 13, and 16 also exhibited antagonist function in fMLF stimulated cells (Table 7). Furthermore, capping group 6 inhibited MPO release at concentrations of 10 uM indicating that it is not a non-binding ligand but rather a potential antagonist. Although capping group 14 significantly increased the degree of MPO release at concentrations of 10 uM (Table 5), significant inhibition was exhibited when administered at 10 uM in the presence of fMLF (p<0.05). This indicates possible partial agonist function. Known antagonist iso-Boc-MLFK exhib ited similar functional characteristics as these modified peptides by significantly inhibiting fMLF-stimulated MPO release at concentrations of 10 uM. It should be noted that MPO release data for capping groups 2, 3, 4 and 17 was not included because internal standard antagonist iso-BocMLFK did not exhibit typical inhibition of MPO release as was seen in other assays.

site-directed mutagenesis define a novel domain for interaction with G-proteins. *J.Biol.Chem.*, 270, 28010–28013.

ASWANIKUMAR S., CORCORAN B., SCHIFFMANN E., DAY A. R., FREER R. J., SHOWELL H. J. & BECKER E. L. (1977). Demonstration of a receptor on rabbit neutrophils for chemotactic peptides. *Biochem.Biophys.Res.Commun.*, 74, 810–817.

TABLE 7

Effect of fMLF amine capping groups on myeloperoxidase release in elicited rat PMNs co-stimulated with 0.1 uM fMLF

| % Control MPO release (0.1 uM fMLF) | Capping Group # | Chemical Identification | % Control MPO release (1 uM capping group + 0.1 uM fMLF) | % Control MPO Release (10 uM capping group + 0.1 uM fMLF) | n |
|---|---|---|---|---|---|
| 291.8 ± 33.0 | 6 | N,N-diethylcarbamyl | 283.3 ± 25.1 | 249.9 ± 6.2 | 2 |
| 155.7 ± 28.5 | 10 | N-phenyl,N-methylcarbamyl | 171.2 ± 6.3 | 121.3 ± 23.9 | 2 |
| 155.7 ± 28.5 | 13 | Adamantylcarbonyl | 131.6 ± 30.9 | 128.6 ± 40.9 | 2 |
| 324.6 ± 4.6 | 14 | 2-quinoxazoyl | 323.2 ± 16.8 | 239.8 ± 9.0 | 2 |
| 155.7 ± 28.5 | 16 | Fluorenylmethylcarbonyl | 161.7 ± 6.2 | 108.9 ± 28.5 | 2 |
| 324.6 ± 4.6 | 18 | N,N-diphenylcarbamoyl | 321.6 ± 8.6 | 185.9 ± 15.7 | 1 |
| 212.0 ± 58.8 | | iso-BocMLFK | 215.4 ± 66.3 | 179.9 ± 50.6 | 3 |

Control wells consisted of elicited rat PMNs without any additional ligand and fMLF was administered at 0.1 uM. In every case, fMLF significantly increased the release of myeloperoxidase in relation to control samples in all cases ($p < 0.05$). A dose-dependent decrease in myeloperoxidase release was observed in fMLF-stimulated PMNs upon administration of all capping groups with significant inhibition occurring at 10 uM ($p < 0.05$). Data is expressed as mean % control ± S.E.M. and n values represent samples performed in quadruplicate.

3.4 Binding of fMLF Amine Capping Groups

Figure 8:
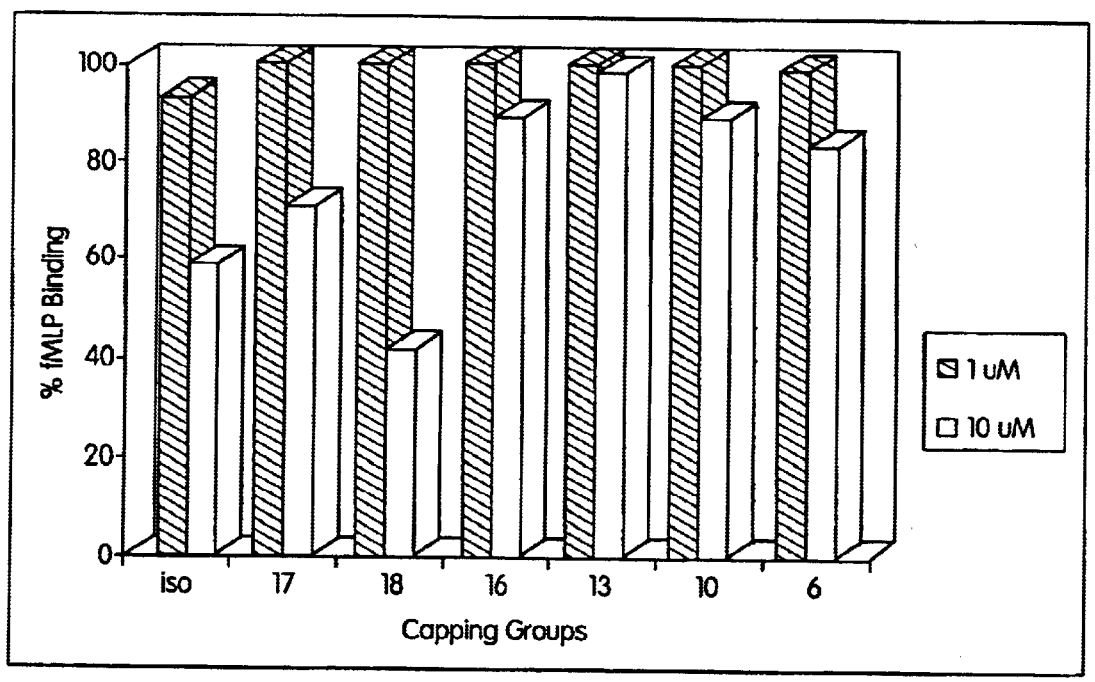
FIG. 8 is a bar graph showing competition Binding of N-terminal modified peptide NleLFK to elicited rat PMNs. Modified peptides were administered at 1 uM and 10 uM concentrations in the presence of 6 nM ³H-fMLF. The iso refers to administration of known antagonist iso-BocMLFK. Data is expressed as mean % control with standard errors being <15% in all cases (n=1, performed in quadruplicate).

As determined by saturation analysis 6nM $^3$H-fMLF was used in competition assays. Competition binding analysis of potential antagonists and modest agonist compounds identified in functional screens indicate that peptide modifications of the N-terminus with cyclopropylcarbonyl (17) or N,N-diphenylcarbamyl (18) groups do not nullify binding affinity (FIG. 8). Moreover, at concentrations of 10 uM, these peptides inhibited $^3$H-fMLF binding to a degree comparable with known antagonist iso-BocMLFK. In particular, this data should be noted for capping group modification 17 since the available functional data with PMNs lacking fMLF stimulation implies that it may be an antagonist or potentially a non-binding ligand. Therefore, additional binding data pertaining to the capping group modification 17 suggests that this peptide may be an antagonist Other peptides modifications such as with capping groups 6, 10, 13 and 16 did not significantly decrease the amount of $^3$H-fMLF binding indicating relatively low binding affinity. However, these peptides did exhibit significant inhibition of MPO release at the 10 uM concentration in fMLF stimulated PMNs (Table 6).

Although the invention has been described with preferred embodiments, it is to be understood that modifications may be resorted to as will be apparent to those skilled in the art. Such modifications and variations are to be considered within the purview and scope of the present invention.

Reference List

ALI H., RICHARDSON R. M., TOMHAVE E. D., DIDSBURY J. R. & SNYDERMAN R. (1993). Differences in phosphorylation of formylpeptide and C5a chemoattractant receptors correlate with differences in desensitization. *J.Biol.Chem.*, 268, 24247–24254.

AMATRUDA T. T., DRAGAS-GRAONIC S., HOLMES R. & PEREZ H. D. (1995). Signal transduction by the formyl peptide receptor. Studies using chimeric receptors and BABICH J. W., SOLOMON H., PIKE M. C., KROON D., GRAHAM W., ABRAMS M. J., TOMPKINS R. G., RUBIN R. H. & FISCHMAN A. J. (1993). Technetium-99m-labeled hydrazino nicotinamide derivatized chemotactic peptide analogs for imaging focal sites of bacterial infection. *J.Nucl.Med.*, 34, 1964–1974.

BABICH J. W., GRAHAM W., BARROW S. A., DRAGO-TAKES S. C., TOMPKINS R. G., RUBIN R. H. & FISCHMAN A. J. (1993). Technetium-99m-labeled chemotactic peptides: comparison with indium-111-labeled white blood cells for localizing acute bacterial infection in the rabbit *J.Nucl.Med.*, 34, 2176–2181.

BABICH J. W., TOMPKINS R. G., GRAHAM W., BARROW S. A. & FISCHMAN A. J. (1997). Localization of radiolabeled chemotactic peptide at focal sites of *Escherichia coli* infection in rabbits: evidence for a receptor-specific mechanism [see comments]. *J.Nucl. Med.*, 38,1316–1322.

BAGGIOLINI M., BOULAY F., BADWEY J. A. & CURNUTTE J. T. (1993). Activation of neutrophil leukocytes: chemoattractant receptors and respiratory burst. *FASEB J.*, 7, 1004–1010.

BENTWOOD B. J. & HENSON P. M. (1980). The sequential release of granule constituterits from human neutrophils. *J.Immunol.*, 124, 855–862.

BOULAY F., TARDIF M., BROUCHON L. & VIGNAIS P. (1990). The human N-formylpeptide receptor. Characterization of two cDNA isolates and evidence for a new subfamily of G-protein-coupled receptors. *Biochemistry*, 29, 11123–11133.

CARP, H. (1982). Mitochondrial N-formylmethionyl proteins as chemoattractants for neutrophils. *J. Exp. Med.*, 155, 264–275.

CHATHAM W. W., TURKIEWICZ A. & BLACKBURN W.D. J. (1994). Determinants of neutrophil HOCl generation: ligand-dependent responses and the role of surface adhesion. *J.Leukoc.Biol.*, 56, 654–680.

CHEN Q., BANICK P. D. & THOM S. R. (1996). Functional inhibition of rat polymorphonuclear leukocyte B2 integrins by hyperbaric oxygen is associated with impaired cGMP synthesis. *J.Pharmacol.Exp.Ther.*, 276, 929–933.

DAY A. R., PINON D., MUTHUKUMARASWAMY N. & FREER R. J. (1980). Synthesis of several chemotactic peptide antagonists. *Peptides*, 1, 289–291.

DERIAN C. K, SOLOMON H. F., HIGGINS J. D., BEBLAVY M. J., SANTULLI R. J., BRIDGER G. J., PIKE M. C., KROON D. J. & FISCHMAN A. J. (1996). Selective inhibition of N-formylpeptide-induced neutrophil activation by carbamate-modified peptide analogues. *Biochemistry*, 35, 1265–1269.

DILLON S. B., VERGHESE M. W. & SNYDERMAN R. (1988). Signal transduction in cells following binding of chemoattractants to membrane receptors. *Vichows Arch. B.Cell Pathol.Incl.Mol.Pathol.*, 55, 65–80.

ENGLISH D. & LUKENS J. N. (1983). Regulation of neutrophil inflammatory mediator release: chemotactic peptide activation of stimulus-dependent cytotoxicity. *J.Immunol.*, 130, 850–856.

FAY S. P., DOMALEWSKI M. D. & SKLAR L. A. (1993). Evidence for protonation in the human neutrophil formyl peptide receptor binding pocket. *Biochemistry*, 32, 1627–1631.

FISCHMAN, A. J., BABICH, J. W., & RUBIN, R. H. (1994). Infection imaging with technetium-99m-labeled chemotactic peptide analogs. *Semin. Nuc. Med.*, 24, 154–168.

FISCHMAN A. J., PIKE M. C., KROON D., FUCELLO A. J., REXINGER D., TEN K. C., WILKINSON R., RUBIN R. H. & STRAUSS H. W. (1991). Imaging focal sites of bacterial infection in rats with indium-111-labeled chemotactic peptide analogs [see comments]. *J.Nucl.Med.*, 32, 483–491.

FOLLIN P., JOHANSSON A. & DAHLGREN C. (1991). Intracellular production of reactive oxygen species in human neutrophils following activation by the soluble stimuli FMLP, dioctanoylglycerol and ionomycin. *Cell Biochem.Funct.*, 9, 29–37.

FREER R. J., DAY A. R., RADDING J. A., SCHIFFMANN E., ASWANIKUMAR S., SHOWELL H. J. & BECKER E. L. (1980). Further studies on the structural requirements for synthetic peptide chemoattractants. *Biochemistry*, 19, 2404–2410.

FREER R. J., DAY A. R., MUTHUKUMARASWAMY N., PINON D., WU A., SHOWELL H. J. & BECKER E. L. (1982). Formyl peptide chemoattractants: a model of the receptor on rabbit neutrophils. *Biochemistry*, 21, 257–263.

GAO J. L, BECKER EL., FREER R. J., MUTHUKUMARASWAMY N. & MURPHY P. M. (1994). A high potency nonformylated peptide agonist for the phagocyte N-formylpeptide chemotactic receptor. *J.Exp.Med.*, 180, 2191–2197.

HAMPTON M. B., KETTLE A. J. & WINTERBOURN C. C. (1996). Involvement of superoxide and myeloperoxidase in oxygen-dependent killing of Staphylococcus aureus by neutrophils. *Infect.Immun.*, 64, 3512–3517.

HIGGINS J. D., BRIDGER G. J., DERIAN C. K., BEBLAVY M. J., HERNANDEZ P. E., GAUL F. E., ABRAMS M. J., PIKE M. C. & SOLOMON H. F. (1996). N-terminus urea-substituted chemotactic pepbdes: new potent agonists and antagonists toward the neutrophil fMLF receptor. *J.Med.Chem.*, 39, 1013–1015.

HO P. P., YOUNG A. L. & SOUTHARD G. L. (1978). Methyl ester of N-formylmethionyl-leucyl-phenylalanine: chemotactic responses of human blood monocytes and inhibition of gold compounds. *Arthrtis Rheum.*, 21, 133–136.

HOFFMAN J. F., KEIL M. L., RICCOBENE T. A., OMANN G. M. & LINDERMAN J. J. (1996a). Interconverting receptor states at 4 degrees C. for the neutrophil N-formyl peptide receptor. *Biochemistry*, 35, 13047–13055.

JESAITIS A. J., NAEMURA J. R., SKLAR L. A., COCHRANE C. G. & PAINTER R. G. (1984). Rapid modulation of N-formyl chemotactic peptide receptors on the surface of human granulocytes: formation of high-affinity ligand-receptor complexes in transient association with cytoskeleton. *J.Cell Biol.*, 98, 1378–1387.

JOHANSSON B., WYMANN M. P., HOLMGREN-PETERSON K. & MAGNUSSON K. E. (1993). N-formyl peptide receptors in human neutrophils display distinct membrane distribution and lateral mobility when labeled with agonist and antagonist. *J.Cell Biol.*, 121, 1281–1289.

KALMAR, J & VAN DYKE, T. (1994). Effect of Bacterial Products on Neutrophil Chemotaxis. *Meth. Enzym.*, 236, 58–87.

KANAMORI Y., NIWA M., KOHNO K., AL-ESSA L. Y., MATSUNO H., KOZAWA O. & UEMATSU T. (1997). Migration of neutrophils from blood to tissue: alteration of modulatory effects of prostanoid on superoxide generation in rabbits and humans. *Life Sci.*, 60,1407–1417.

KORCHAK H. M., WILKENFELD C., RICH A. M., RADIN A. R., VIENNE K & RUTHERFORD L. E. (1984). Stimulus response coupling in the human neutrophil, Differential requirements for receptor occupancy in neutrophil responses to a chemoattractant. *J.Biol.Chem.*, 259, 7439–7445.

LUSCINSKAS, F. W., CYBULSKY, M. I., KIELY, J. M., PECKINS, C. S., DAVIS, V. M. & GIMBRONE, M. A. (1991). Cytokine-activated human endothelial monolayers support enhanced neutrophil transmigration via a mechanism involving both endothelial leukocyte adhesion molecule-1 and intercellular adhesion molecule-1. *J. Immunol.*, 146, 1617–1625.

MARASCO W. A., FANTONE J. C., FREER R. J. & WARD P. A. (1983). Characterization of the rat neutrophil formyl peptide chemotaxis receptor. *Am.J.Pathol.*, 111, 273–281.

MCKAY D. A., KUSEL J. R. & WILKINSON P. C. (1991). Studies of chemotactic factor-induced polarity in human neutrophils. Lipid mobility, receptor distribution and the time-sequence of polarization. *J.Cell Sci.*, 100 (Pt 3), 473–479.

MIETTINEN H. M., MILLS J. S., GRIPENTROG J. M., DRATZ E. A., GRANGER B. L. & JESAITIS A. J. (1997). The ligand binding site of the fomnyl peptide receptor maps in the transmembrane region. *J.Immunol.*, 159, 4045–4054.

MIYASAKI K. T., SONG J. P. & MURTHY R. K. (1991). Secretion of myeloperoxidase isoforms by human neutrophils. *Anal.Biochem.*, 193, 38–44.

MUELLER H., WEINGARTEN R., RANSNAS L. A., BOKOCH G. M. & SKLAR L. A. (1991). Differential amplification of antagonistic receptor pathways in neutrophils. *J.Blol.Chem.*, 266, 12939–12943.

NIEDEL J., WILKINSON S. & CUATRECASAS P. (1979). Receptor-mediated uptake and degradation of 125l-chemotactic peptide by human neutrophils. *J.Biol.Chem.*, 254, 10700–10706.

NUNOI H., ENDO F., CHIKAZAWA S. & MATSUDA I. (1985). Regulation of receptors and digestive activity toward synthesized formyl-chemotactic peptide in human polymorphonuclear leukocytes. *Blood*, 66, 106–114.

PAINTER R. G. & AIKEN M. L. (1995). Regulation of N-formyl-methionyl-leucyl-phenylalanine receptor recycling by surface membrane neutral endopeptidase-mediated degradation of ligand. *J.Leukoc.Biol.*, 58, 468–476.

PALMBLAD J. (1984). The role of granulocytes in inflammation. *Scand.J.RheumatoL*, 13,163–172.

PEREZ H. D., ELFMAN F., MARDER S., LOBO E. a IVES H. E. (1989). Fornyl peptide-induced chemotaxis of human polymorphonuclear leukocytes does not require either marked changes in cytosolic calcium or specific granule discharge. Role of formyl peptide receptor reexpression (or recycling). *J.Clin.Invest.*, 83, 1963–1970.

PROSSNITZ E. R. & YE R. D. (1997). The N-formyl peptide receptor a model for the study of chemoattractant receptor structure and function. *Pharnacol.Ther.*, 74, 73–102.

PROSSNITZ E. R. (1997). Desensitization of N-formylpeptide receptor-mediated activation is dependent upon receptor phosphorylation. *J.Biol.Chem.*, 272, 15213–15219.

RADEL S. J., GENCO R. J. & DE N. E. (1994). Structural and functional characterization of the human formyl peptide receptor ligand-binding region. *Infect.Immun.*, 62, 1726–1732.

REMES J., PETAJA-REPO U. & RAJANIEMI H. (1994). Internalization of N-formyl peptide chemotactic receptor-ligand complex by human neutrophils. The role of the receptor's 2-kDa external domain and carbohydrates. *J.Recept.Res.*, 14, 47–62.

REMES J. J., PETAJA-REPO U. E. & RAJANIEMI H. J. (1991). Rat and human neutrophil N-formyl-peptide chemotactic receptors. Species difference in the glycosylation of similar 35–38 kDa polypeptide cores. *Biochem.J.*, 277 (Pt 1), 67–72.

RIBEIRO R. A., SOUZA-FILHO M. V., SOUZA M. H., OLIVEIRA S. H., COSTA C. H., CUNHA F. Q. & FERREIRA H. S. (1997). Role of resident mast cells and macrophages in the neutrophil migration induced by LTB4, fMLP and C5a des arg. *Int.Arch.Allergy Immunol.*, 112, 27–35.

SCHIFFMANN, E., CORCORAN, B. A. and WHALE, S. M. (1975). N-formylmethionylpeptides as chemoattractants for leukocytes. *Proc. Natl. Acad. Sci. USA* 72,1059–1062.

SCHREIBER R. E., PROSSNITZ E. R., YE R. D., COCHRANE C. G. & BOKOCH G. M. (1994). Domains of the human neutrophil N-formyl peptide receptor involved in G protein coupling. Mapping with receptor-derived peptides. *J.Biol.Chem.*, 269, 326–331.

SEPE S. M. & CLARK R. A. (1985). Oxidant membrane injury by the neutrophil myeloperoxidase system. I. Characterization of a liposome model and injury by myeloperoxidase, hydrogen peroxide, and halides. *J.Immunol.*, 134, 1888–1895.

SKALAK R., SKIERCZYNSKI B. A., WUNG S. L., CHIEN S. & USAMI S. (1993). Mechanical models of pseudopod formation. *Blood Cells*, 19, 389–397.

SKLAR L. A., FINNEY D. A., OADES Z. G., JESAITIS A. J., PAINTER R. G. & COCHRANE C. G. (1984). The dynamics of ligandreceptor interactions. Real-time analyses of association, dissociation, and internalization of an N-formyl peptide and its receptors on the human neutrophil. *J.Biol.Chem.*, 259, 5661–5669.

SKLAR L. A., SAYRE J., MCNEIL V. M. & FINNEY D. A. (1985). Competitive binding kinetics in ligand-receptor-compelitor systems. Rate parameters for unlabeled ligands for the formyl peptide receptor. *Mol.Pharmacol.*, 28, 323–330.

SKLAR L. A., FAY S. P., SELIGMANN B. E., FREER R. J., MUTHUKUMARASWAMY N. & MUELLER H. (1990). Fluorescence analysis of the size of a binding pocket of a peptide receptor at natural abundance. *Biochemistry*, 29, 313–316.

SNYDERMAN R. (1983). Pharmacologic manipulation of leukocyte chemotaxds. Present knowledge and future trends. *Am.J.Med.*, 75, 10–18.

SPISANI S., TRANIELLO S., GIULIANI A. L., TORRINI I., PAGANI Z. G., PAGLIALUNGA P. M., GAVUZZO E., MAZZA F., POCHETTI G. & WCENTE G. (1992). New chemotactc peptide analogs vwth high biological activity for human neutrophils. *Biochem.Int.*, 26, 1125–1135.

SRINIVASAN R., BUCHWEITZ J. P. & GANEY P. E. (1997). Alteration by flutamide of neutrophil response to stimulation. Implications for tissue injury. *Biochem.Pharnacol.*, 53, 1179–1185.

TAE, H. J., GROSSMANN, M. and INHAE, J. (1998). G protein-coupled receptors. Diversity of receptor-ligand interactions. *J. Biol. Chem.*, 273 (28), 17299–17302.

TARDIF M., MERY L., BROUCHON L. & BOULAY F. (1993). Agonist-dependent phosphorylation of N-formylpeptide and activation peptide from the fifth component of C (C5a) chemoattractant receptors in differentiated HL60 cells. *J.Immunol.*, 150, 3534–3545.

TONIOLO C., CRISMA M., MORETTO V., FREER R. J. & BECKER E. L. (1990). N alpha-formylated and tert-butyloxycarbonylated Phe-(Leu-Phe)n and (Leu-Phe)n peptides as agonists and antagonists of the chemotacbic formylpeptide receptor of the rabbit peritoneal neutrophil. *Biochim.Biophys.Acta*, 1034, 67–72.

TONIOLO C., CRISMA M. & BECKER E. L. (1990). Replacement of the N alpha-blocking group in the formyl-methionyl tripeptide chemoattractant: an insight into the mode of binding at the receptor on rabbit neutrophils. *Farmaco.*, 45, 921–925.

VALLABHAJOUSULA, S. (1997). Technetium-99m-Labeled Chemotactic Peptides: Specific for imaging Infection? *J. Nuc. Med.*, 38, 1322–1326.

VAN DER LAKEN C J, BOERMAN O. C., OYEN W. J., VAN DE VEN M T, EDWARDS D. S., BARRETT J. A., VAN DER MEER J W & CORSTENS F. H. (1997). Technetium-99m-labeled chemotactic peptides in acute infection and sterile inflammation [see comments]. *J.Nucd.Med.*, 38, 1310–1315.

WANG J. P., TSAO L. T., RAUNG S. L. & LIN C. N. (1997). Investigation of the inhibitory effect of broussochalcone A on respiratory burst in neutxphils. *Eur.J.Pharmacol.*, 320, 201–208.

WEISS, S. J., PEPPIN, G., ORTIZ, X., RAGSDALE, C., TEST, S. T. (1983). Oxidative autoactivation of latent collagenase by human neutrophils. *Science*, 227, 747–749.

WILLIAMS L. T., SNYDERMAN R., PIKE M. C. & LEFKOWITZ R. J. (1977). Specific receptor sites for chemotactic peptides on human polymorphonuclear leukocytes. *Proc.Nati.Acad.Sci.U.S.A.*, 74, 1204–1208.

WINTERBOURN C. C., PICHORNER H. & KETTLE A. J. (1997). Myeloperoxidase-dependent generation of a tyrosine peroxide by neutrophils. *Arch.Biochem.Biophys.*, 338, 15–21.

WONG, E, FAUCONNIER, T., BENNETT, S., VALLIANT, J., NGUYEN, T., LAU, F., LU, L. F. L., POLLAK, A., BELL, R. A. and THORNBACK, J. R. (1997). Rhenium (V) and Technetium(V) Oxo Complexes of an $N_2N'S$ Peptide Chelator Evidence of Interconversion between the Syn and Anti Conformations. *Inorg. Chem.*, 36, 5799–5808.

What is claimed is:

1. A combinatorial library for obtaining compounds that target sites of inflammation comprising a mixture of molecules of the following formula I:

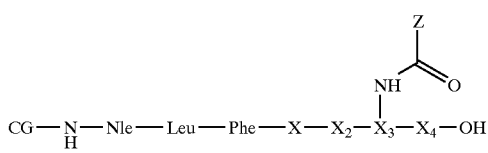

wherein CG is a capping group selected from the group consisting of

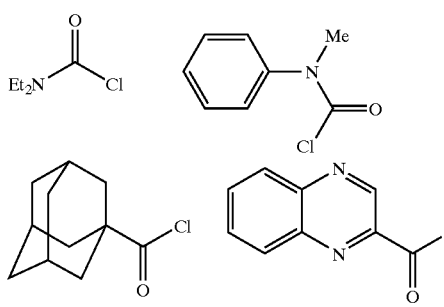

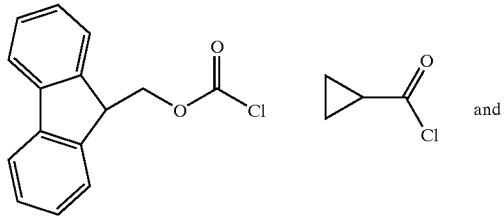 and

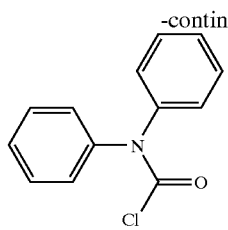

-continued wherein Cl represents the point of attachment of the capping group:

X, X$_2$, X$_3$ and X$_4$ are amino acids selected from natural and unnatural amino acids; Z is a chelator capable of complexing a radionuclide metal or a chelator complexed to a radionuclide metal, X$_3$ being a site of attachment for said chelator.

2. A combinatorial library according to claim 1 wherein the molecules have the following formula II:

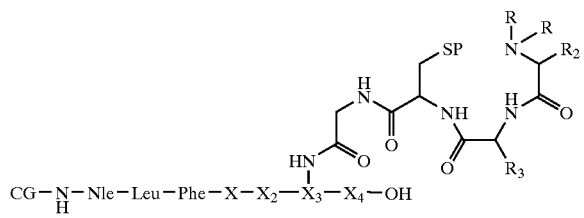

wherein R, and R$_2$ is a linear or branched, saturated or unsaturated C$_{1-6}$ aklyl chain that is optionally interrupted by one or two heteroatoms selected from N, O, and S; and is optionally substituted by at least one group selected from hydroxyl, amino, carboxyl, C$_{1-6}$ alkyl, aryl and C(O) R; R$_3$ is selected from H; alkyl; an alkyl substituted by a group selected from amino, aminoacyl, carboxyl, guaniginyl, hydroxyl, thiol, phenyl, phenolyl, indolyl, and imidazolyl.

3. A combinatorial library according to claim 1 wherein said compounds target N-formyl-methionyl-leucyl-phenylalanine (fMLF) receptor.

4. A combinatorial library according to claim 1 wherein X3 is Lys and X4 is Gly.

5. A combinatorial library according to claim 3 wherein the library comprises mixtures wherein X corresponds to an amino acid sequence selected from the group consisting of (Phe, Asp, Leu), (Trp, Ser, Tyr), (Glu, His, Lys) and (Asn, Arg, Val) and X2 corresponds to an amino acid sequence selected from the group consisting of (Trp, Ser, Tyr), (Glu, His, Lys) and (Asn, Arg, Val).

* * * * *